United States Patent
Wehba et al.

(10) Patent No.: US 12,036,390 B2
(45) Date of Patent: Jul. 16, 2024

(54) SYSTEM AND METHOD FOR CONFIGURING A RULE SET FOR MEDICAL EVENT MANAGEMENT AND RESPONSES

(71) Applicant: ICU Medical, Inc., San Clemente, CA (US)

(72) Inventors: Steven R. Wehba, Carlsbad, CA (US); Timothy L. Ruchti, Gurnee, IL (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

(21) Appl. No.: 18/300,839

(22) Filed: Apr. 14, 2023

(65) Prior Publication Data

US 2023/0321351 A1 Oct. 12, 2023

Related U.S. Application Data

(60) Continuation of application No. 17/238,780, filed on Apr. 23, 2021, now Pat. No. 11,654,237, which is a
(Continued)

(51) Int. Cl.
*A61M 31/00* (2006.01)
*A61M 5/172* (2006.01)
(Continued)

(52) U.S. Cl.
CPC .......... *A61M 5/1723* (2013.01); *G16H 20/17* (2018.01); *G16H 40/20* (2018.01); *G16H 40/67* (2018.01);
(Continued)

(58) Field of Classification Search
CPC ..... A61M 5/1723; G16H 40/20; G16H 50/20; G06F 19/3468
(Continued)

(56) References Cited

U.S. PATENT DOCUMENTS 4,024,864 A 5/1977 Davies et al.
4,055,175 A 10/1977 Clemens et al.
(Continued)

FOREIGN PATENT DOCUMENTS

CA 2 060 151 8/1997
CA 2 125 300 10/1999
(Continued)

OTHER PUBLICATIONS

Ahn et al., "Towards Scalable Authentication in Health Services", Eleventh IEEE International Workshops on Enabling Technologies: Infrastructure for Collaborative Enterprises, Jun. 2002, pp. 83-88.
(Continued)

*Primary Examiner* — Phillip A Gray
(74) *Attorney, Agent, or Firm* — Knobbe, Martens, Olson & Bear, LLP

(57) ABSTRACT

A system and method to configure a rule set used in connection with a medical monitoring system for monitoring patients and patient care equipment, especially medication delivery pumps, based on a variety of conditions and parameters associated with monitored biometric information and equipment information and for providing user-defined responses to those conditions and parameters.

20 Claims, 5 Drawing Sheets

Related U.S. Application Data continuation of application No. 16/266,622, filed on Feb. 4, 2019, now Pat. No. 11,013,861, which is a continuation of application No. 15/467,903, filed on Mar. 23, 2017, now Pat. No. 10,238,801, which is a continuation of application No. 13/586,615, filed on Aug. 15, 2012, now Pat. No. 9,604,000, which is a division of application No. 12/761,107, filed on Apr. 15, 2010, now Pat. No. 8,271,106.

(60) Provisional application No. 61/170,205, filed on Apr. 17, 2009.

(51) Int. Cl.
    *G16H 20/17*     (2018.01)
    *G16H 40/20*     (2018.01)
    *G16H 40/67*     (2018.01)
    *G16H 50/20*     (2018.01)
    *A61M 5/14*     (2006.01)
    *A61M 5/142*     (2006.01)

(52) U.S. Cl.
CPC ..... *G16H 50/20* (2018.01); *A61M 2005/1405* (2013.01); *A61M 2005/14208* (2013.01); *A61M 2005/14296* (2013.01); *A61M 2205/18* (2013.01); *A61M 2205/3553* (2013.01); *A61M 2205/3561* (2013.01); *A61M 2205/50* (2013.01); *A61M 2205/52* (2013.01); *A61M 2230/04* (2013.01); *A61M 2230/06* (2013.01); *A61M 2230/201* (2013.01); *A61M 2230/202* (2013.01); *A61M 2230/205* (2013.01); *A61M 2230/30* (2013.01); *A61M 2230/42* (2013.01); *A61M 2230/50* (2013.01)

(58) Field of Classification Search
USPC .......................................................... 604/66
See application file for complete search history.

(56) References Cited

U.S. PATENT DOCUMENTS

| | | |
|---|---|---|
| 4,151,845 A | 5/1979 | Clemens |
| 4,213,454 A | 7/1980 | Shim |
| 4,240,438 A | 12/1980 | Updike et al. |
| 4,280,494 A | 7/1981 | Cosgrove et al. |
| 4,308,866 A | 1/1982 | Jeliffe |
| 4,370,983 A | 2/1983 | Lichtenstein et al. |
| 4,373,527 A | 2/1983 | Fischell |
| 4,392,849 A | 7/1983 | Petre et al. |
| 4,395,259 A | 7/1983 | Prestele et al. |
| 4,457,751 A | 7/1984 | Rodler |
| 4,464,170 A | 8/1984 | Clemens |
| 4,469,481 A | 9/1984 | Kobayashi |
| 4,475,901 A | 10/1984 | Kraegen et al. |
| 4,494,950 A | 1/1985 | Fischell |
| 4,498,843 A | 2/1985 | Schneider et al. |
| 4,515,584 A | 5/1985 | Abe et al. |
| 4,526,568 A | 7/1985 | Clemens et al. |
| 4,529,401 A | 7/1985 | Leslie et al. |
| 4,543,955 A | 10/1985 | Schroeppel |
| 4,551,133 A | 11/1985 | Zegers de Beyl et al. |
| 4,553,958 A | 11/1985 | LeCocq |
| 4,559,037 A | 12/1985 | Franetzki et al. |
| 4,613,937 A | 9/1986 | Batty |
| 4,624,661 A | 11/1986 | Arimond |
| 4,633,878 A | 1/1987 | Bombardieri |
| 4,634,426 A | 1/1987 | Kamen |
| 4,634,427 A | 1/1987 | Hannula et al. |
| 4,674,652 A | 6/1987 | Aten et al. |
| 4,676,776 A | 6/1987 | Howson et al. |
| 4,679,562 A | 7/1987 | Luksha |
| 4,685,903 A | 8/1987 | Cable et al. |
| 4,695,954 A | 9/1987 | Rose |
| 4,696,671 A | 9/1987 | Epstein et al. |
| 4,714,462 A | 12/1987 | DiDomenico |
| 4,722,734 A | 2/1988 | Kolin |
| 4,730,849 A | 3/1988 | Siegel |
| 4,731,051 A | 3/1988 | Fischell |
| 4,741,732 A | 5/1988 | Crankshaw et al. |
| 4,756,706 A | 7/1988 | Kerns et al. |
| 4,776,842 A | 10/1988 | Franetzki et al. |
| 4,785,969 A | 11/1988 | McLaughlin |
| 4,803,625 A | 2/1989 | Fu et al. |
| 4,835,372 A | 5/1989 | Gombrich et al. |
| 4,838,275 A | 6/1989 | Lee |
| 4,838,856 A | 6/1989 | Mulreany et al. |
| 4,838,857 A | 6/1989 | Strowe et al. |
| 4,854,324 A | 8/1989 | Hirschman et al. |
| 4,857,716 A | 8/1989 | Gombrich et al. |
| 4,858,154 A | 8/1989 | Anderson et al. |
| 4,898,578 A | 2/1990 | Rubalcaba, Jr. |
| 4,908,017 A | 3/1990 | Howson et al. |
| 4,933,873 A | 6/1990 | Kaufman et al. |
| 4,943,279 A | 7/1990 | Samiotes et al. |
| 4,946,439 A | 8/1990 | Eggers |
| 4,953,745 A | 9/1990 | Rowlett |
| 4,978,335 A | 12/1990 | Arthur, III |
| 5,000,739 A | 3/1991 | Kulisz et al. |
| 5,010,473 A | 4/1991 | Jacobs |
| 5,014,698 A | 5/1991 | Cohen |
| 5,016,172 A | 5/1991 | Dessertine |
| 5,026,084 A | 6/1991 | Paisfield |
| 5,034,004 A | 7/1991 | Crankshaw |
| 5,041,086 A | 8/1991 | Koenig et al. |
| 5,058,161 A | 10/1991 | Weiss |
| 5,078,683 A | 1/1992 | Sancoff et al. |
| 5,084,828 A | 1/1992 | Kaufman et al. |
| 5,088,981 A | 2/1992 | Howson et al. |
| 5,097,505 A | 3/1992 | Weiss |
| 5,100,380 A | 3/1992 | Epstein et al. |
| 5,102,392 A | 4/1992 | Sakai et al. |
| 5,104,374 A | 4/1992 | Bishko et al. |
| 5,109,850 A | 5/1992 | Blanco et al. |
| 5,131,816 A | 7/1992 | Brown |
| 5,142,484 A | 8/1992 | Kaufman et al. |
| 5,153,827 A | 10/1992 | Coutre et al. |
| 5,157,640 A | 10/1992 | Backner |
| 5,161,222 A | 11/1992 | Montejo et al. |
| 5,177,993 A | 1/1993 | Beckman et al. |
| 5,181,910 A | 1/1993 | Scanlon |
| 5,190,522 A | 3/1993 | Wocicki et al. |
| 5,199,439 A | 4/1993 | Zimmerman et al. |
| 5,200,891 A | 4/1993 | Kehr et al. |
| 5,216,597 A | 6/1993 | Beckers |
| 5,221,268 A | 6/1993 | Barton et al. |
| 5,230,061 A * | 7/1993 | Welch .................. G05B 19/052 700/49 |
| 5,243,982 A | 9/1993 | Möstl et al. |
| 5,244,463 A | 9/1993 | Cordner, Jr. et al. |
| 5,249,260 A | 9/1993 | Nigawara et al. |
| 5,256,156 A | 10/1993 | Kern et al. |
| 5,256,157 A | 10/1993 | Samiotes et al. |
| 5,261,702 A | 11/1993 | Mayfield |
| 5,317,506 A | 5/1994 | Coutre et al. |
| 5,319,355 A | 6/1994 | Russek |
| 5,319,363 A | 6/1994 | Welch et al. |
| 5,330,634 A | 7/1994 | Wong et al. |
| 5,338,157 A | 8/1994 | Blomquist |
| 5,341,476 A | 8/1994 | Lowell |
| 5,364,346 A | 11/1994 | Schrezenmeir |
| 5,366,346 A | 11/1994 | Danby |
| 5,368,562 A | 11/1994 | Blomquist et al. |
| 5,373,454 A | 12/1994 | Kanda et al. |
| 5,376,070 A | 12/1994 | Purvis et al. |
| 5,378,231 A | 1/1995 | Johnson et al. |
| 5,389,071 A | 2/1995 | Kawahara et al. |
| 5,389,078 A | 2/1995 | Zalesky et al. |
| 5,417,222 A | 5/1995 | Dempsey et al. |
| 5,423,748 A | 6/1995 | Uhala |
| 5,429,602 A | 7/1995 | Hauser |
| 5,431,627 A | 7/1995 | Pastrone et al. |

(56) References Cited

U.S. PATENT DOCUMENTS

| | | |
|---|---|---|
| 5,432,777 A | 7/1995 | Le Boudec et al. |
| 5,445,621 A | 8/1995 | Poli et al. |
| 5,447,164 A | 9/1995 | Shaya et al. |
| 5,455,851 A | 10/1995 | Chaco et al. |
| 5,461,365 A | 10/1995 | Schlager et al. |
| 5,464,392 A | 11/1995 | Epstein et al. |
| 5,465,082 A | 11/1995 | Chaco |
| 5,485,408 A | 1/1996 | Blomquist |
| 5,486,286 A | 1/1996 | Peterson et al. |
| 5,493,430 A | 2/1996 | Lu et al. |
| 5,496,273 A | 3/1996 | Pastrone et al. |
| 5,505,828 A | 4/1996 | Wong et al. |
| 5,507,288 A | 4/1996 | Bocker et al. |
| 5,507,786 A | 4/1996 | Morgan et al. |
| 5,508,499 A | 4/1996 | Ferrario |
| 5,515,713 A | 5/1996 | Saugues et al. |
| 5,520,637 A | 5/1996 | Pager et al. |
| 5,522,798 A | 6/1996 | Johnson et al. |
| 5,547,470 A | 8/1996 | Johnson et al. |
| 5,554,013 A | 9/1996 | Owens et al. |
| 5,562,615 A | 10/1996 | Nassif |
| 5,577,169 A | 11/1996 | Prezioso |
| 5,582,323 A | 12/1996 | Kurtenbach |
| 5,582,593 A | 12/1996 | Hultman |
| 5,594,786 A | 1/1997 | Chaco et al. |
| 5,598,519 A | 1/1997 | Narayanan |
| 5,620,608 A | 4/1997 | Rosa et al. |
| 5,630,710 A | 5/1997 | Tune et al. |
| 5,636,044 A | 6/1997 | Yuan et al. |
| 5,643,212 A | 7/1997 | Coutre et al. |
| 5,651,775 A | 7/1997 | Walker et al. |
| 5,658,131 A | 8/1997 | Aoki et al. |
| 5,658,250 A | 8/1997 | Blomquist et al. |
| 5,665,065 A | 9/1997 | Colman et al. |
| 5,669,877 A | 9/1997 | Blomquist |
| 5,672,154 A | 9/1997 | Sillén et al. |
| 5,681,285 A | 10/1997 | Ford et al. |
| 5,685,844 A | 11/1997 | Marttila |
| 5,687,717 A | 11/1997 | Halpern et al. |
| 5,689,229 A | 11/1997 | Chaco et al. |
| 5,697,899 A | 12/1997 | Hillman et al. |
| 5,699,509 A | 12/1997 | Gary et al. |
| 5,713,350 A | 2/1998 | Yokota et al. |
| 5,713,856 A | 2/1998 | Eggers et al. |
| 5,718,562 A | 2/1998 | Lawless et al. |
| 5,719,761 A | 2/1998 | Gatti et al. |
| 5,733,259 A | 3/1998 | Valcke et al. |
| 5,738,102 A | 4/1998 | Lemelson |
| 5,744,027 A | 4/1998 | Connell et al. |
| 5,752,621 A | 5/1998 | Passamante |
| 5,754,111 A | 5/1998 | Garcia |
| 5,764,034 A | 6/1998 | Bowman et al. |
| 5,764,159 A | 6/1998 | Neftel et al. |
| 5,772,635 A | 6/1998 | Dastur et al. |
| 5,774,865 A | 6/1998 | Glynn |
| 5,778,256 A | 7/1998 | Darbee |
| 5,778,345 A | 7/1998 | McCartney |
| 5,781,442 A | 7/1998 | Engleson et al. |
| 5,782,805 A | 7/1998 | Meinzer et al. |
| 5,788,669 A | 8/1998 | Peterson |
| 5,797,515 A | 8/1998 | Liff et al. |
| 5,800,387 A | 9/1998 | Duffy et al. |
| 5,814,015 A | 9/1998 | Gargano et al. |
| 5,822,544 A | 10/1998 | Chaco et al. |
| 5,822,715 A | 10/1998 | Worthington et al. |
| 5,827,179 A | 10/1998 | Lichter et al. |
| 5,832,448 A | 11/1998 | Brown |
| 5,836,910 A | 11/1998 | Duffy et al. |
| 5,850,344 A | 12/1998 | Conkright |
| 5,867,821 A | 2/1999 | Ballantyne et al. |
| 5,870,733 A | 2/1999 | Bass et al. |
| 5,871,465 A | 2/1999 | Vasko |
| 5,873,731 A | 2/1999 | Predergast |
| 5,885,245 A | 3/1999 | Lynch et al. |
| 5,897,493 A | 4/1999 | Brown |
| 5,897,498 A | 4/1999 | Canfield, II et al. |
| 5,910,252 A | 6/1999 | Truitt et al. |
| 5,912,818 A | 6/1999 | McGrady et al. |
| 5,915,240 A | 6/1999 | Karpf |
| 5,920,054 A | 7/1999 | Uber, III |
| 5,920,263 A | 7/1999 | Huttenhoff et al. |
| 5,924,074 A | 7/1999 | Evans |
| 5,931,764 A | 8/1999 | Freeman et al. |
| 5,935,099 A | 8/1999 | Peterson et al. |
| 5,935,106 A | 8/1999 | Olsen |
| 5,941,846 A | 8/1999 | Duffy et al. |
| 5,956,501 A | 9/1999 | Brown |
| 5,957,885 A | 9/1999 | Bollish et al. |
| 5,960,085 A | 9/1999 | de la Huerga |
| 5,961,448 A | 10/1999 | Swenson et al. |
| 5,967,559 A | 10/1999 | Abramowitz |
| 5,971,594 A | 10/1999 | Sahai et al. |
| 5,975,081 A | 11/1999 | Hood et al. |
| 5,990,838 A | 11/1999 | Burns et al. |
| 5,997,476 A | 12/1999 | Brown |
| 6,000,828 A | 12/1999 | Leet |
| 6,003,006 A | 12/1999 | Colella et al. |
| 6,012,034 A | 1/2000 | Hamparian et al. |
| 6,017,318 A | 1/2000 | Gauthier et al. |
| 6,021,392 A | 2/2000 | Lester et al. |
| 6,024,539 A | 2/2000 | Blomquist |
| 6,024,699 A | 2/2000 | Surwit et al. |
| 6,032,155 A | 2/2000 | de la Huerga |
| 6,032,676 A | 3/2000 | Moore |
| 6,039,251 A | 3/2000 | Holowko et al. |
| 6,070,761 A | 6/2000 | Bloom et al. |
| 6,073,106 A | 6/2000 | Rozen et al. |
| 6,104,295 A | 8/2000 | Gaisser et al. |
| 6,112,182 A | 8/2000 | Akers et al. |
| 6,112,323 A | 8/2000 | Meizlik et al. |
| RE36,871 E | 9/2000 | Epstein et al. |
| 6,115,390 A | 9/2000 | Chuah |
| 6,122,536 A | 9/2000 | Sun et al. |
| 6,126,637 A | 10/2000 | Kriesel et al. |
| 6,135,949 A | 10/2000 | Russo et al. |
| 6,150,942 A | 11/2000 | O'Brien |
| 6,151,643 A | 11/2000 | Cheng et al. |
| 6,157,914 A | 12/2000 | Seto et al. |
| 6,159,147 A | 12/2000 | Lichter et al. |
| 6,167,567 A | 12/2000 | Chiles et al. |
| 6,182,667 B1 | 2/2001 | Hanks et al. |
| 6,189,105 B1 | 2/2001 | Lopes |
| 6,195,589 B1 | 2/2001 | Ketcham |
| 6,208,974 B1 | 3/2001 | Campbell et al. |
| 6,222,323 B1 | 4/2001 | Yamashita et al. |
| 6,223,440 B1 | 5/2001 | Rashman |
| 6,226,277 B1 | 5/2001 | Chuah |
| 6,227,371 B1 | 5/2001 | Song |
| 6,234,176 B1 | 5/2001 | Domae et al. |
| 6,241,704 B1 | 6/2001 | Peterson et al. |
| 6,248,067 B1 | 6/2001 | Causey, III et al. |
| 6,249,705 B1 | 6/2001 | Snell |
| 6,257,265 B1 | 7/2001 | Brunner et al. |
| 6,259,355 B1 | 7/2001 | Chaco et al. |
| 6,269,340 B1 | 7/2001 | Ford et al. |
| 6,270,455 B1 | 8/2001 | Brown |
| 6,271,813 B1 | 8/2001 | Palalau |
| 6,277,072 B1 | 8/2001 | Bardy |
| 6,280,380 B1 | 8/2001 | Bardy |
| 6,283,761 B1 | 9/2001 | Joao |
| 6,285,665 B1 | 9/2001 | Chuah |
| 6,292,860 B1 | 9/2001 | Cochcroft, Jr. |
| 6,312,378 B1 | 11/2001 | Bardy |
| 6,327,254 B1 | 12/2001 | Chuah |
| 6,330,008 B1 | 12/2001 | Razdow et al. |
| 6,339,718 B1 | 1/2002 | Zatezalo et al. |
| 6,346,886 B1 | 2/2002 | de la Huerga |
| 6,363,282 B1 | 3/2002 | Nichols et al. |
| 6,371,719 B1 | 4/2002 | Hildebrandt |
| 6,377,548 B1 | 4/2002 | Chuah |
| 6,388,951 B1 | 5/2002 | Matsumoto et al. |
| 6,406,426 B1 | 6/2002 | Reuss et al. |
| 6,408,330 B1 | 6/2002 | de la Huerga |
| 6,418,334 B1 | 7/2002 | Unger et al. |

(56) References Cited

U.S. PATENT DOCUMENTS

| | | |
|---|---|---|
| 6,427,088 B1 | 7/2002 | Bowman et al. |
| 6,428,483 B1 | 8/2002 | Carlebach |
| 6,442,432 B2 | 8/2002 | Lee |
| 6,469,991 B1 | 10/2002 | Chuah |
| 6,475,180 B2 | 11/2002 | Peterson et al. |
| 6,482,158 B2 | 11/2002 | Mault |
| 6,485,418 B2 | 11/2002 | Yasushi et al. |
| 6,494,694 B2 | 12/2002 | Lawless et al. |
| 6,494,831 B1 | 12/2002 | Koritzinsky |
| 6,497,680 B1 | 12/2002 | Holst et al. |
| 6,514,460 B1 | 2/2003 | Fendrock |
| 6,517,482 B1 | 2/2003 | Eiden et al. |
| 6,519,569 B1 | 2/2003 | White et al. |
| 6,520,930 B2 | 2/2003 | Critchlow et al. |
| 6,540,672 B1 | 4/2003 | Simonsen et al. |
| 6,542,902 B2 | 4/2003 | Dulong et al. |
| 6,544,212 B2 | 4/2003 | Galley et al. |
| 6,544,228 B1 | 4/2003 | Heitmeier |
| 6,546,350 B1 | 4/2003 | Hartmann et al. |
| 6,551,276 B1 | 4/2003 | Mann et al. |
| 6,554,798 B1 | 4/2003 | Mann et al. |
| 6,558,320 B1 | 5/2003 | Causey et al. |
| 6,558,351 B1 | 5/2003 | Steil et al. |
| 6,565,509 B1 | 5/2003 | Say et al. |
| 6,567,416 B1 | 5/2003 | Chuah |
| 6,571,294 B2 | 5/2003 | Simmon et al. |
| 6,572,542 B1 | 6/2003 | Houben et al. |
| 6,572,545 B2 | 6/2003 | Knobbe et al. |
| 6,578,002 B1 | 6/2003 | Derzay et al. |
| 6,581,117 B1 | 6/2003 | Klein et al. |
| 6,587,034 B1 | 7/2003 | Heiman et al. |
| 6,589,229 B1 | 7/2003 | Connelly et al. |
| 6,599,281 B1 | 7/2003 | Struys et al. |
| 6,602,191 B2 | 8/2003 | Quy |
| 6,605,072 B2 | 8/2003 | Struys et al. |
| 6,628,809 B1 | 9/2003 | Rowe et al. |
| 6,631,353 B1 | 10/2003 | Davis et al. |
| 6,640,246 B1 | 10/2003 | Gardy, Jr. et al. |
| 6,641,533 B2 | 11/2003 | Causey, III et al. |
| 6,647,299 B2 | 11/2003 | Bourget |
| 6,652,455 B1 | 11/2003 | Kocher |
| 6,653,937 B2 | 11/2003 | Nelson et al. |
| 6,659,947 B1 | 12/2003 | Carter et al. |
| 6,669,630 B1 | 12/2003 | Joliat et al. |
| 6,671,563 B1 | 12/2003 | Engleson et al. |
| 6,673,033 B1 | 1/2004 | Sciulli et al. |
| 6,674,403 B2 | 1/2004 | Gray et al. |
| 6,681,003 B2 | 1/2004 | Linder et al. |
| 6,689,091 B2 | 2/2004 | Bui et al. |
| 6,692,241 B2 | 2/2004 | Watanabe et al. |
| 6,694,191 B2 | 2/2004 | Starkweather et al. |
| 6,694,334 B2 | 2/2004 | DuLong et al. |
| 6,721,286 B1 | 4/2004 | Williams et al. |
| 6,721,582 B2 | 4/2004 | Trepagnier et al. |
| 6,725,200 B2 | 4/2004 | Rost |
| 6,731,989 B2 | 5/2004 | Engleson et al. |
| 6,740,072 B2 | 5/2004 | Starkweather et al. |
| 6,751,651 B2 | 6/2004 | Crockett |
| 6,752,787 B1 | 6/2004 | Causey, III et al. |
| 6,753,830 B2 | 6/2004 | Gelbman |
| 6,758,810 B2 | 7/2004 | Lebel et al. |
| 6,773,396 B2 | 8/2004 | Flach et al. |
| 6,774,786 B1 | 8/2004 | Havekost et al. |
| 6,775,577 B2 | 8/2004 | Cmkovich et al. |
| 6,780,156 B2 | 8/2004 | Haueter et al. |
| 6,790,198 B1 | 9/2004 | White et al. |
| 6,792,470 B2 | 9/2004 | Hakenberg et al. |
| 6,796,956 B2 | 9/2004 | Hartlaub et al. |
| 6,799,149 B2 | 9/2004 | Hartlaub |
| 6,809,653 B1 | 10/2004 | Mann et al. |
| 6,811,534 B2 | 11/2004 | Bowman, IV et al. |
| 6,816,605 B2 | 11/2004 | Rowe et al. |
| 6,839,753 B2 | 1/2005 | Biondi et al. |
| 6,852,104 B2 | 2/2005 | Blomquist |
| 6,859,134 B1 | 2/2005 | Heiman et al. |
| 6,871,211 B2 | 3/2005 | Labounty et al. |
| 6,873,268 B2 | 3/2005 | Lebel et al. |
| 6,876,303 B2 | 4/2005 | Reeder et al. |
| 6,885,881 B2 | 4/2005 | Leonhardt |
| 6,891,525 B2 | 5/2005 | Ogoro |
| 6,892,278 B2 | 5/2005 | Ebergen |
| 6,899,695 B2 | 5/2005 | Herrera |
| 6,915,170 B2 | 7/2005 | Engleson et al. |
| 6,923,763 B1 | 8/2005 | Kovatchev et al. |
| 6,924,781 B1 | 8/2005 | Gelbman |
| 6,928,338 B1 | 8/2005 | Buchser et al. |
| 6,928,490 B1 | 8/2005 | Bucholz et al. |
| 6,936,029 B2 | 8/2005 | Mann et al. |
| 6,945,954 B2 | 9/2005 | Hochman et al. |
| 6,948,492 B2 | 9/2005 | Wemeling et al. |
| 6,958,677 B1 | 10/2005 | Carter |
| 6,958,691 B1 | 10/2005 | Anderson et al. |
| 6,958,705 B2 | 10/2005 | Lebel et al. |
| 6,961,448 B2 | 11/2005 | Nichols et al. |
| 6,969,352 B2 | 11/2005 | Chiang et al. |
| 6,969,865 B2 | 11/2005 | Duchon et al. |
| 6,974,437 B2 | 12/2005 | Lebel et al. |
| 6,979,326 B2 | 12/2005 | Mann et al. |
| 6,980,958 B1 | 12/2005 | Surwit et al. |
| 6,985,870 B2 | 1/2006 | Martucci et al. |
| 6,986,347 B2 | 1/2006 | Hickle |
| 6,997,880 B2 | 2/2006 | Carlebach et al. |
| 6,997,920 B2 | 2/2006 | Mann et al. |
| 6,998,984 B1 | 2/2006 | Zittrain |
| 7,016,752 B1 | 3/2006 | Ruben et al. |
| 7,017,293 B2 | 3/2006 | Riley |
| 7,025,743 B2 | 4/2006 | Mann et al. |
| 7,029,455 B2 | 4/2006 | Flaherty |
| 7,038,584 B2 | 5/2006 | Carter |
| 7,060,031 B2 | 6/2006 | Webb et al. |
| 7,060,059 B2 | 6/2006 | Keith et al. |
| 7,069,552 B2 | 6/2006 | Lindberg et al. |
| 7,072,725 B2 | 7/2006 | Bristol et al. |
| 7,079,035 B2 | 7/2006 | Bock et al. |
| 7,092,943 B2 | 8/2006 | Roese et al. |
| 7,096,072 B2 | 8/2006 | Engleson et al. |
| 7,099,809 B2 | 8/2006 | Dori |
| 7,103,419 B2 | 9/2006 | Engleson et al. |
| 7,103,578 B2 | 9/2006 | Beck et al. |
| 7,107,106 B2 | 9/2006 | Engleson et al. |
| 7,108,680 B2 | 9/2006 | Rohr et al. |
| 7,109,878 B2 | 9/2006 | Mann et al. |
| 7,114,002 B1 | 9/2006 | Okumura et al. |
| 7,117,041 B2 | 10/2006 | Engleson et al. |
| 7,136,645 B2 | 11/2006 | Hanson et al. |
| 7,137,964 B2 | 11/2006 | Flaherty |
| 7,142,190 B2 | 11/2006 | Martinez |
| 7,150,741 B2 | 12/2006 | Erickson et al. |
| 7,153,289 B2 | 12/2006 | Vasko |
| 7,154,397 B2 | 12/2006 | Zerhusen et al. |
| 7,156,807 B2 | 1/2007 | Carter et al. |
| 7,158,030 B2 | 1/2007 | Chung |
| 7,161,484 B2 | 1/2007 | Tsoukalis et al. |
| 7,167,755 B2 | 1/2007 | Seeberger et al. |
| 7,167,920 B2 | 1/2007 | Traversat |
| 7,171,277 B2 | 1/2007 | Engleson et al. |
| 7,171,492 B1 | 1/2007 | Borella et al. |
| 7,181,493 B2 | 2/2007 | English et al. |
| 7,185,288 B2 | 2/2007 | McKeever |
| 7,193,514 B2 | 3/2007 | Ritson |
| 7,197,025 B2 | 3/2007 | Chuah |
| 7,201,734 B2 | 4/2007 | Hickle |
| 7,204,823 B2 | 4/2007 | Estes et al. |
| 7,213,009 B2 | 5/2007 | Pestotnik |
| 7,216,802 B1 | 5/2007 | de la Huerga |
| 7,220,240 B2 | 5/2007 | Struys et al. |
| 7,224,979 B2 | 5/2007 | Singhal et al. |
| 7,229,430 B2 | 6/2007 | Hickle et al. |
| 7,230,529 B2 | 6/2007 | Ketcherside |
| 7,236,936 B2 | 6/2007 | White et al. |
| 7,238,164 B2 | 7/2007 | Childers et al. |
| 7,247,154 B2 | 7/2007 | Hickle |
| 7,248,239 B2 | 7/2007 | Dowling |
| 7,250,856 B2 | 7/2007 | Havekost et al. |

(56) References Cited

U.S. PATENT DOCUMENTS

| | | |
|---|---|---|
| 7,255,683 B2 | 8/2007 | Vanderveen et al. |
| 7,256,888 B2 | 8/2007 | Staehr et al. |
| 7,258,534 B2 | 8/2007 | Fathallah et al. |
| 7,263,213 B2 | 8/2007 | Rowe |
| 7,267,664 B2 | 9/2007 | Rizzo |
| 7,267,665 B2 | 9/2007 | Steil et al. |
| 7,275,156 B2 | 9/2007 | Balfanz et al. |
| 7,278,983 B2 | 10/2007 | Ireland et al. |
| 7,289,815 B2 | 10/2007 | Gfeller et al. |
| 7,289,948 B1 | 10/2007 | Mohri |
| 7,293,107 B1 | 11/2007 | Hanson et al. |
| 7,295,119 B2 | 11/2007 | Rappaport et al. |
| 7,295,556 B2 | 11/2007 | Roese et al. |
| 7,301,451 B2 | 11/2007 | Hastings |
| 7,308,300 B2 | 12/2007 | Toews et al. |
| 7,315,825 B2 | 1/2008 | Rosenfeld et al. |
| 7,319,386 B2 | 1/2008 | Collins, Jr. et al. |
| 7,324,000 B2 | 1/2008 | Zittrain et al. |
| 7,327,705 B2 | 2/2008 | Fletcher et al. |
| 7,343,224 B2 | 3/2008 | DiGianfilippo et al. |
| 7,346,025 B2 | 3/2008 | Bryson |
| 7,347,836 B2 | 3/2008 | Peterson et al. |
| 7,354,420 B2 | 4/2008 | Steil et al. |
| 7,369,897 B2 | 5/2008 | Boveja et al. |
| 7,369,948 B1 | 5/2008 | Ferenczi et al. |
| 7,383,088 B2 | 6/2008 | Spinelli et al. |
| 7,384,410 B2 | 6/2008 | Eggers et al. |
| 7,398,183 B2 | 7/2008 | Holland et al. |
| 7,398,279 B2 | 7/2008 | Muno, Jr. et al. |
| 7,399,277 B2 | 7/2008 | Saidara et al. |
| 7,402,153 B2 | 7/2008 | Steil et al. |
| 7,420,472 B2 | 9/2008 | Tran |
| 7,432,807 B2 | 10/2008 | Schmitt |
| 7,436,454 B2 | 10/2008 | Yamaguchi et al. |
| 7,447,643 B1 | 11/2008 | Olson |
| 7,454,314 B2 | 11/2008 | Holland et al. |
| 7,457,804 B2 | 11/2008 | Uber, III et al. |
| 7,464,040 B2 | 12/2008 | Joao |
| 7,469,213 B1 | 12/2008 | Rao |
| 7,471,994 B2 | 12/2008 | Ford et al. |
| 7,483,756 B2 | 1/2009 | Engleson et al. |
| 7,489,808 B2 | 2/2009 | Gerder |
| 7,490,021 B2 | 2/2009 | Holland et al. |
| 7,490,048 B2 | 2/2009 | Joao |
| 7,491,187 B2 | 2/2009 | Van Den Berghe et al. |
| 7,519,905 B2 | 4/2009 | Kougiouris et al. |
| 7,523,401 B1 | 4/2009 | Aldridge |
| 7,524,304 B2 | 4/2009 | Genosar |
| 7,551,078 B2 | 6/2009 | Carlson |
| 7,559,321 B2 | 7/2009 | Wermeling et al. |
| 7,565,197 B2 | 7/2009 | Haulbrich et al. |
| 7,572,230 B2 | 8/2009 | Neumann et al. |
| 7,578,802 B2 | 8/2009 | Hickle |
| 7,621,009 B2 | 11/2009 | Elhabashy |
| D606,533 S | 12/2009 | De Jong et al. |
| 7,636,718 B1 | 12/2009 | Steen et al. |
| 7,640,172 B2 | 12/2009 | Kuth |
| 7,645,258 B2 | 1/2010 | White et al. |
| 7,647,237 B2 | 1/2010 | Malave et al. |
| 7,662,124 B2 | 2/2010 | Duchon et al. |
| 7,668,731 B2 | 2/2010 | Martucci et al. |
| 7,671,733 B2 | 3/2010 | McNeal et al. |
| 7,678,071 B2 | 3/2010 | Lebel et al. |
| 7,687,678 B2 | 3/2010 | Jacobs |
| 7,697,994 B2 | 4/2010 | VanDanacker et al. |
| 7,698,239 B2 | 4/2010 | Lieuallen |
| 7,705,727 B2 | 4/2010 | Pestotnik |
| 7,724,147 B2 | 5/2010 | Brown et al. |
| 7,739,126 B1 | 6/2010 | Cave |
| 7,746,218 B2 | 6/2010 | Collins, Jr. |
| 7,766,873 B2 | 8/2010 | Moberg et al. |
| 7,776,029 B2 | 8/2010 | Whitehurst et al. |
| 7,776,031 B2 | 8/2010 | Hartlaub et al. |
| 7,785,313 B2 | 8/2010 | Mastrototaro |
| 7,788,369 B2 | 8/2010 | McAllen et al. |
| 7,806,852 B1 | 10/2010 | Jurson |
| 7,806,886 B2 | 10/2010 | Kanderian, Jr. et al. |
| 7,826,981 B2 | 11/2010 | Goode, Jr. et al. |
| 7,835,927 B2 | 11/2010 | Schlotterbeck et al. |
| 7,836,314 B2 | 11/2010 | Chieu |
| 7,856,276 B2 | 12/2010 | Ripart et al. |
| 7,860,583 B2 | 12/2010 | Condurso et al. |
| 7,864,771 B2 | 1/2011 | Tavares et al. |
| 7,868,754 B2 | 1/2011 | Salvat, Jr. |
| 7,871,394 B2 | 1/2011 | Halbert et al. |
| 7,886,231 B2 | 2/2011 | Hopermann et al. |
| 7,895,053 B2 | 2/2011 | Holland et al. |
| 7,896,842 B2 | 3/2011 | Palmroos et al. |
| 7,899,546 B2 | 3/2011 | Sieracki et al. |
| 7,905,710 B2 | 3/2011 | Wang et al. |
| 7,920,061 B2 | 4/2011 | Klein et al. |
| 7,933,780 B2 | 4/2011 | de la Huerga |
| 7,938,796 B2 | 5/2011 | Moubayed |
| 7,945,452 B2 | 5/2011 | Fathallah et al. |
| 7,974,714 B2 | 7/2011 | Hoffberg |
| 7,976,508 B2 | 7/2011 | Hoag |
| 7,996,241 B2 | 8/2011 | Zak |
| 8,034,026 B2 | 10/2011 | Grant |
| 8,038,593 B2 | 10/2011 | Friedman et al. |
| 8,048,040 B2 | 11/2011 | Kiani |
| 8,060,576 B2 | 11/2011 | Chan et al. |
| 8,065,161 B2 | 11/2011 | Howard et al. |
| 8,066,672 B2 | 11/2011 | Mandro |
| 8,075,514 B2 | 12/2011 | Butterfield et al. |
| 8,078,983 B2 | 12/2011 | Davis et al. |
| 8,082,018 B2 | 12/2011 | Duchon et al. |
| 8,082,312 B2 | 12/2011 | Chan et al. |
| 8,095,692 B2 | 1/2012 | Mehta et al. |
| 8,126,730 B2 | 2/2012 | Dicks et al. |
| 8,147,448 B2 | 4/2012 | Sundar et al. |
| 8,149,131 B2 | 4/2012 | Blomquist |
| 8,169,914 B2 | 5/2012 | Bajpai |
| 8,171,094 B2 | 5/2012 | Chan et al. |
| 8,172,798 B2 | 5/2012 | Hungerford et al. |
| 8,185,322 B2 | 5/2012 | Schroeder et al. |
| 8,195,478 B2 | 6/2012 | Petersen et al. |
| 8,206,350 B2 | 6/2012 | Mann et al. |
| 8,219,413 B2 | 7/2012 | Martinez et al. |
| 8,231,578 B2 | 7/2012 | Fathallah et al. |
| 8,234,128 B2 | 7/2012 | Martucci et al. |
| 8,267,892 B2 | 9/2012 | Spencer et al. |
| 8,271,106 B2 | 9/2012 | Wehba et al. |
| 8,287,495 B2 | 10/2012 | Michaud et al. |
| 8,291,337 B2 | 10/2012 | Gannin et al. |
| 8,298,184 B2 | 10/2012 | DiPerna et al. |
| 8,312,272 B1 | 11/2012 | Serenyl et al. |
| 8,352,290 B2 | 1/2013 | Bartz et al. |
| 8,359,338 B2 | 1/2013 | Butterfield et al. |
| 8,380,536 B2 | 2/2013 | Howard et al. |
| 8,387,112 B1 | 2/2013 | Ranjan et al. |
| 8,394,077 B2 | 3/2013 | Jacobson et al. |
| 8,398,592 B2 | 3/2013 | Leibner-Druska |
| 8,403,908 B2 | 3/2013 | Jacobson et al. |
| 8,435,206 B2 | 5/2013 | Evans et al. |
| 8,449,523 B2 | 5/2013 | Brukalo et al. |
| 8,452,953 B2 | 5/2013 | Buck et al. |
| 8,453,645 B2 | 6/2013 | Figueiredo et al. |
| 8,472,630 B2 | 6/2013 | Konrad et al. |
| 8,480,648 B2 | 7/2013 | Burnett et al. |
| 8,489,427 B2 | 7/2013 | Simpson et al. |
| 8,494,879 B2 | 7/2013 | Davis et al. |
| 8,504,179 B2 | 8/2013 | Blomquist |
| 8,517,990 B2 | 8/2013 | Teel et al. |
| 8,518,021 B2 | 8/2013 | Stewart et al. |
| 8,543,416 B2 | 9/2013 | Palmroos et al. |
| 8,551,038 B2 | 10/2013 | Tsoukalis et al. |
| 8,560,345 B2 | 10/2013 | Wehba et al. |
| 8,567,681 B2 | 10/2013 | Borges et al. |
| 8,577,692 B2 | 11/2013 | Silkaitis et al. |
| 8,579,884 B2 | 11/2013 | Lanier et al. |
| 8,626,530 B1 | 1/2014 | Tran et al. |
| 8,655,676 B2 | 2/2014 | Wehba et al. |
| 8,660,860 B2 | 2/2014 | Wehba et al. |
| 8,662,388 B2 | 3/2014 | Belkin |

(56) References Cited

U.S. PATENT DOCUMENTS

| | | |
|---|---|---|
| 8,666,769 B2 | 3/2014 | Butler et al. |
| 8,667,293 B2 | 3/2014 | Birtwhistle et al. |
| 8,687,811 B2 | 4/2014 | Nierzwick et al. |
| 8,700,421 B2 | 4/2014 | Feng et al. |
| 8,731,960 B2 | 5/2014 | Butler et al. |
| 8,768,719 B2 | 7/2014 | Wehba et al. |
| 8,771,251 B2 | 7/2014 | Ruchti et al. |
| 8,777,894 B2 | 7/2014 | Butterfield et al. |
| 8,777,895 B2 | 7/2014 | Hsu et al. |
| 8,799,012 B2 | 8/2014 | Butler et al. |
| 8,876,793 B2 | 11/2014 | Ledford et al. |
| 8,886,316 B1 | 11/2014 | Juels |
| 8,922,330 B2 | 12/2014 | Moberg et al. |
| 8,936,565 B2 | 1/2015 | Chawla |
| 8,945,043 B2 | 2/2015 | Lee et al. |
| 8,952,794 B2 | 2/2015 | Blomquist et al. |
| 8,959,617 B2 | 2/2015 | Newlin et al. |
| 8,998,100 B2 | 4/2015 | Halbert et al. |
| 9,026,370 B2 | 5/2015 | Rubalcaba et al. |
| 9,069,887 B2 | 6/2015 | Gupta et al. |
| 9,077,544 B2 | 7/2015 | Baker et al. |
| 9,089,642 B2 | 7/2015 | Murphy et al. |
| 9,114,217 B2 | 8/2015 | Sur et al. |
| 9,123,077 B2 | 9/2015 | Silkaitis et al. |
| 9,192,712 B2 | 11/2015 | DeBelser et al. |
| 9,240,002 B2 | 1/2016 | Hume et al. |
| 9,292,692 B2 | 3/2016 | Wallrabenstein |
| 9,302,035 B2 | 4/2016 | Marseille et al. |
| 9,313,154 B1 | 4/2016 | Son |
| 9,381,296 B2 | 7/2016 | Arrizza et al. |
| 9,393,362 B2 | 7/2016 | Cozmi et al. |
| 9,430,655 B1 | 8/2016 | Stockton et al. |
| 9,483,615 B2 | 11/2016 | Roberts |
| 9,498,583 B2 | 11/2016 | Sur et al. |
| 9,539,383 B2 | 1/2017 | Kohlbrecher |
| 9,572,923 B2 | 2/2017 | Howard et al. |
| 9,594,875 B2 | 3/2017 | Arrizza et al. |
| 9,604,000 B2 | 3/2017 | Wehba et al. |
| 9,641,432 B2 | 5/2017 | Jha et al. |
| 9,649,431 B2 | 5/2017 | Gray et al. |
| 9,662,436 B2 | 5/2017 | Belkin et al. |
| 9,690,909 B2 | 6/2017 | Stewart et al. |
| 9,707,341 B2 | 7/2017 | Dumas, III et al. |
| 9,717,845 B2 | 8/2017 | Istoc |
| 9,724,470 B2 | 8/2017 | Day et al. |
| 9,764,082 B2 | 9/2017 | Day et al. |
| 9,886,550 B2 | 2/2018 | Lee et al. |
| 9,943,269 B2 | 4/2018 | Muhsin et al. |
| 9,967,739 B2 | 5/2018 | Proennecke et al. |
| 9,971,871 B2 | 5/2018 | Arrizza et al. |
| 9,995,611 B2 | 6/2018 | Ruchti et al. |
| 10,022,498 B2 | 7/2018 | Ruchti et al. |
| 10,042,986 B2 | 8/2018 | Ruchti et al. |
| 10,046,112 B2 | 8/2018 | Oruklu et al. |
| 10,166,328 B2 | 1/2019 | Oruklu et al. |
| 10,173,008 B2 | 1/2019 | Simpson et al. |
| 10,233,179 B2 | 3/2019 | Ng et al. |
| 10,238,799 B2 | 3/2019 | Kohlbrecher |
| 10,238,801 B2 | 3/2019 | Wehba et al. |
| 10,242,060 B2 | 3/2019 | Butler et al. |
| 10,300,194 B2 | 5/2019 | Day et al. |
| 10,311,972 B2 | 6/2019 | Kohlbrecher et al. |
| 10,314,974 B2 | 6/2019 | Day et al. |
| 10,333,843 B2 | 6/2019 | Jha et al. |
| 10,341,866 B1 | 7/2019 | Spencer et al. |
| 10,430,761 B2 | 10/2019 | Hume et al. |
| 10,434,246 B2 | 10/2019 | Silkaitis et al. |
| 10,453,157 B2 | 10/2019 | Kamen et al. |
| 10,463,788 B2 | 11/2019 | Day |
| 10,516,536 B2 | 12/2019 | Rommel |
| 10,617,815 B2 | 4/2020 | Day et al. |
| 10,646,651 B2 | 5/2020 | Day et al. |
| 10,681,207 B1 | 6/2020 | Johnson et al. |
| 10,692,595 B2 | 6/2020 | Xavier et al. |
| 10,740,436 B2 | 8/2020 | Moskal et al. |
| 10,741,280 B2 | 8/2020 | Xavier et al. |
| 10,757,219 B2 | 8/2020 | Moskal |
| 10,765,799 B2 | 9/2020 | Belkin et al. |
| 10,799,632 B2 | 10/2020 | Kohlbrecher |
| 10,812,380 B2 | 10/2020 | Jha et al. |
| 10,861,592 B2 | 12/2020 | Xavier et al. |
| 10,898,641 B2 | 1/2021 | Day et al. |
| 10,950,339 B2 | 3/2021 | Xavier et al. |
| 10,964,428 B2 | 3/2021 | Xavier et al. |
| 11,013,861 B2 | 5/2021 | Wehba et al. |
| 11,037,668 B2 | 6/2021 | Ruchti et al. |
| 11,052,193 B2 | 7/2021 | Day et al. |
| 11,139,058 B2 | 10/2021 | Xavier et al. |
| 11,151,290 B2 | 10/2021 | Karakoyunlu et al. |
| 11,152,108 B2 | 10/2021 | Xavier et al. |
| 11,152,109 B2 | 10/2021 | Xavier et al. |
| 11,152,110 B2 | 10/2021 | Xavier et al. |
| 11,194,810 B2 | 12/2021 | Butler et al. |
| 11,235,100 B2 | 2/2022 | Howard et al. |
| 11,289,183 B2 | 3/2022 | Kohlbrecher |
| 11,309,070 B2 | 4/2022 | Xavier et al. |
| 11,328,804 B2 | 5/2022 | Xavier et al. |
| 11,328,805 B2 | 5/2022 | Xavier et al. |
| 11,373,753 B2 | 6/2022 | Xavier et al. |
| 11,437,132 B2 | 9/2022 | Xavier et al. |
| 11,470,000 B2 | 10/2022 | Jha et al. |
| 11,483,402 B2 | 10/2022 | Xavier et al. |
| 11,483,403 B2 | 10/2022 | Xavier et al. |
| 11,501,877 B2 | 11/2022 | Kohlbrecher et al. |
| 11,571,508 B2 | 2/2023 | Jacobson et al. |
| 11,574,721 B2 | 2/2023 | Kohlbrecher |
| 11,574,737 B2 | 2/2023 | Dharwad et al. |
| 11,587,669 B2 | 2/2023 | Xavier et al. |
| 11,594,326 B2 | 2/2023 | Xavier et al. |
| 11,605,468 B2 | 3/2023 | Jacobson et al. |
| 11,626,205 B2 | 4/2023 | Arrizza et al. |
| 11,628,246 B2 | 4/2023 | Day et al. |
| 11,628,254 B2 | 4/2023 | Day et al. |
| 11,654,237 B2 | 5/2023 | Wehba et al. |
| 11,670,416 B2 | 6/2023 | Xavier et al. |
| 2001/0016056 A1 | 8/2001 | Westphal et al. |
| 2001/0031944 A1 | 10/2001 | Peterson et al. |
| 2001/0032099 A1 | 10/2001 | Joao |
| 2001/0037060 A1 | 11/2001 | Thompson et al. |
| 2001/0044731 A1 | 11/2001 | Coffman et al. |
| 2001/0048027 A1 | 12/2001 | Walsh |
| 2001/0051787 A1 | 12/2001 | Haller et al. |
| 2001/0056358 A1 | 12/2001 | Dulong et al. |
| 2002/0010595 A1 | 1/2002 | Kapp |
| 2002/0013551 A1 | 1/2002 | Zaitsu et al. |
| 2002/0013723 A1 | 1/2002 | Mise |
| 2002/0015018 A1 | 2/2002 | Shimazu et al. |
| 2002/0019584 A1 | 2/2002 | Schulze et al. |
| 2002/0021700 A1 | 2/2002 | Hata et al. |
| 2002/0026103 A1 | 2/2002 | Norris et al. |
| 2002/0029776 A1 | 3/2002 | Blomquist |
| 2002/0032583 A1 | 3/2002 | Joao |
| 2002/0038206 A1* | 3/2002 | Dori .................... G06F 17/289 703/22 |
| 2002/0040208 A1 | 4/2002 | Flaherty et al. |
| 2002/0040282 A1 | 4/2002 | Bailey et al. |
| 2002/0044043 A1 | 4/2002 | Chaco et al. |
| 2002/0044059 A1 | 4/2002 | Reeder et al. |
| 2002/0082728 A1 | 6/2002 | Mueller et al. |
| 2002/0087115 A1 | 7/2002 | Hartlaub |
| 2002/0087116 A1 | 7/2002 | Hartlaub |
| 2002/0095486 A1 | 7/2002 | Bahl |
| 2002/0103675 A1 | 8/2002 | Vanelli |
| 2002/0123905 A1 | 9/2002 | Goodroe et al. |
| 2002/0143580 A1 | 10/2002 | Bristol et al. |
| 2002/0152239 A1 | 10/2002 | Bautista-Lloyd et al. |
| 2002/0154600 A1 | 10/2002 | Ido et al. |
| 2002/0173702 A1 | 11/2002 | Lebel et al. |
| 2002/0173875 A1 | 11/2002 | Wallace et al. |
| 2002/0194329 A1 | 12/2002 | Alling |
| 2003/0009244 A1 | 1/2003 | Engleson |
| 2003/0013959 A1 | 1/2003 | Grunwald et al. |
| 2003/0014222 A1 | 1/2003 | Klass et al. |
| 2003/0014817 A1 | 1/2003 | Gallant et al. |

(56) References Cited

U.S. PATENT DOCUMENTS

| | | |
|---|---|---|
| 2003/0025602 A1 | 2/2003 | Medema et al. |
| 2003/0028082 A1 | 2/2003 | Thompson |
| 2003/0036683 A1 | 2/2003 | Kehr et al. |
| 2003/0036744 A1 | 2/2003 | Struys et al. |
| 2003/0047126 A1 | 3/2003 | Tomaschko |
| 2003/0050621 A1 | 3/2003 | Lebel et al. |
| 2003/0059750 A1 | 3/2003 | Bindler et al. |
| 2003/0060688 A1 | 3/2003 | Ciarniello et al. |
| 2003/0069963 A1 | 4/2003 | Jayant et al. |
| 2003/0079746 A1 | 5/2003 | Hickle |
| 2003/0097529 A1 | 5/2003 | Arimilli et al. |
| 2003/0104982 A1 | 6/2003 | Wittmann et al. |
| 2003/0105389 A1 | 6/2003 | Noonan et al. |
| 2003/0106553 A1 | 6/2003 | Vanderveen |
| 2003/0115358 A1 | 6/2003 | Yun |
| 2003/0120384 A1 | 6/2003 | Haitin et al. |
| 2003/0125662 A1 | 7/2003 | Bui |
| 2003/0130616 A1 | 7/2003 | Steil |
| 2003/0135087 A1 | 7/2003 | Hickle et al. |
| 2003/0139701 A1 | 7/2003 | White et al. |
| 2003/0140928 A1 | 7/2003 | Bui et al. |
| 2003/0140929 A1 | 7/2003 | Wilkes et al. |
| 2003/0141981 A1 | 7/2003 | Bui et al. |
| 2003/0143746 A1 | 7/2003 | Sage, Jr. |
| 2003/0144878 A1 | 7/2003 | Wilkes et al. |
| 2003/0158749 A1 | 8/2003 | Olchanski et al. |
| 2003/0187338 A1 | 10/2003 | Say et al. |
| 2003/0200116 A1 | 10/2003 | Forrester |
| 2003/0204416 A1 | 10/2003 | Acharya |
| 2003/0204781 A1 | 10/2003 | Peebles et al. |
| 2003/0212364 A1 | 11/2003 | Mann et al. |
| 2003/0212379 A1 | 11/2003 | Bylund et al. |
| 2003/0212821 A1 | 11/2003 | Gillies et al. |
| 2003/0217962 A1 | 11/2003 | Childers et al. |
| 2004/0008123 A1 | 1/2004 | Carrender et al. |
| 2004/0015132 A1 | 1/2004 | Brown |
| 2004/0019607 A1 | 1/2004 | Moubayed et al. |
| 2004/0030323 A1 | 2/2004 | Ullestad et al. |
| 2004/0039257 A1 | 2/2004 | Hickle |
| 2004/0057226 A1 | 3/2004 | Berthou et al. |
| 2004/0064341 A1 | 4/2004 | Langan et al. |
| 2004/0064342 A1 | 4/2004 | Browne et al. |
| 2004/0064435 A1 | 4/2004 | Moubayed et al. |
| 2004/0073811 A1 | 4/2004 | Sanin |
| 2004/0077934 A1 | 4/2004 | Massad |
| 2004/0078231 A1 | 4/2004 | Wilkes et al. |
| 2004/0078236 A1 | 4/2004 | Stoodley et al. |
| 2004/0085186 A1 | 5/2004 | Eveland et al. |
| 2004/0104271 A1 | 6/2004 | Martucci et al. |
| 2004/0122530 A1 | 6/2004 | Hansen |
| 2004/0128162 A1 | 7/2004 | Schlotterbeck et al. |
| 2004/0128163 A1 | 7/2004 | Goodman et al. |
| 2004/0133441 A1 | 7/2004 | Brady et al. |
| 2004/0139004 A1 | 7/2004 | Cohen et al. |
| 2004/0145480 A1 | 7/2004 | Despotis |
| 2004/0147034 A1 | 7/2004 | Gore et al. |
| 2004/0167464 A1 | 8/2004 | Ireland et al. |
| 2004/0167465 A1 | 8/2004 | Kohler |
| 2004/0167804 A1 | 8/2004 | Simpson |
| 2004/0172222 A1 | 9/2004 | Simpson et al. |
| 2004/0172283 A1 | 9/2004 | Vanderveen |
| 2004/0172301 A1 | 9/2004 | Mihai et al. |
| 2004/0172302 A1 | 9/2004 | Martucci et al. |
| 2004/0176667 A1 | 9/2004 | Mihai et al. |
| 2004/0176980 A1 | 9/2004 | Bulitta et al. |
| 2004/0176984 A1 | 9/2004 | White et al. |
| 2004/0181314 A1 | 9/2004 | Zaleski |
| 2004/0189708 A1 | 9/2004 | Larcheveque et al. |
| 2004/0193325 A1 | 9/2004 | Bonderud |
| 2004/0193328 A1 | 9/2004 | Butterfield et al. |
| 2004/0193453 A1 | 9/2004 | Butterfield et al. |
| 2004/0204673 A1 | 10/2004 | Flaherty et al. |
| 2004/0215278 A1 | 10/2004 | Stegink et al. |
| 2004/0220517 A1 | 11/2004 | Starkweather et al. |
| 2004/0225252 A1 | 11/2004 | Gillespie et al. |
| 2004/0236240 A1 | 11/2004 | Kraus et al. |
| 2004/0243438 A1 | 12/2004 | Mintz |
| 2004/0254434 A1 | 12/2004 | Goodnow et al. |
| 2005/0010269 A1 | 1/2005 | Lebel et al. |
| 2005/0020886 A1 | 1/2005 | Hutchinson et al. |
| 2005/0021006 A1 | 1/2005 | Tonnies |
| 2005/0027560 A1 | 2/2005 | Cook |
| 2005/0027567 A1 | 2/2005 | Taha |
| 2005/0038311 A1 | 2/2005 | Kuth |
| 2005/0038669 A1 | 2/2005 | Sachdeva et al. |
| 2005/0038680 A1 | 2/2005 | McMahon |
| 2005/0040226 A1 | 2/2005 | Al-Sheikh |
| 2005/0043620 A1 | 2/2005 | Fallows et al. |
| 2005/0049910 A1 | 3/2005 | Lancaster et al. |
| 2005/0055242 A1 | 3/2005 | Bello et al. |
| 2005/0055244 A1 | 3/2005 | Mullan et al. |
| 2005/0065465 A1 | 3/2005 | Lebel et al. |
| 2005/0065817 A1 | 3/2005 | Mihai et al. |
| 2005/0075544 A1 | 4/2005 | Shapiro et al. |
| 2005/0080801 A1 | 4/2005 | Kothandaraman et al. |
| 2005/0086071 A1 | 4/2005 | Fox, Jr. et al. |
| 2005/0086072 A1 | 4/2005 | Fox |
| 2005/0088704 A1 | 4/2005 | Vaschillo et al. |
| 2005/0090808 A1 | 4/2005 | Malave et al. |
| 2005/0099624 A1 | 5/2005 | Staehr |
| 2005/0102162 A1 | 5/2005 | Blumenfeld |
| 2005/0102165 A1 | 5/2005 | Oshita et al. |
| 2005/0102167 A1 | 5/2005 | Kapoor |
| 2005/0102669 A1 | 5/2005 | Marney et al. |
| 2005/0107923 A1 | 5/2005 | Vanderveen |
| 2005/0108057 A1 | 5/2005 | Cohen et al. |
| 2005/0117529 A1 | 6/2005 | Ramos-Escano |
| 2005/0119788 A1 | 6/2005 | Engleson et al. |
| 2005/0119914 A1 | 6/2005 | Batch |
| 2005/0131739 A1 | 6/2005 | Rabinowitz et al. |
| 2005/0135306 A1 | 6/2005 | McAllen et al. |
| 2005/0137522 A1 | 6/2005 | Aoki |
| 2005/0137573 A1 | 6/2005 | McLaughlin |
| 2005/0138428 A1 | 6/2005 | McAllen et al. |
| 2005/0154769 A1 | 7/2005 | Eckart et al. |
| 2005/0160057 A1 | 7/2005 | Wefers et al. |
| 2005/0171503 A1 | 8/2005 | Van Den Berghe et al. |
| 2005/0171815 A1 | 8/2005 | Vanderveen |
| 2005/0177096 A1 | 8/2005 | Bollish et al. |
| 2005/0177395 A1 | 8/2005 | Blomquist |
| 2005/0182306 A1 | 8/2005 | Sloan |
| 2005/0182355 A1 | 8/2005 | Bui |
| 2005/0187950 A1 | 8/2005 | Parker |
| 2005/0192557 A1 | 9/2005 | Brauker et al. |
| 2005/0197554 A1 | 9/2005 | Polcha |
| 2005/0197621 A1 | 9/2005 | Poulsen et al. |
| 2005/0210037 A1 | 9/2005 | Wefers et al. |
| 2005/0216479 A1 | 9/2005 | Wefers et al. |
| 2005/0216480 A1 | 9/2005 | Wefers et al. |
| 2005/0223045 A1 | 10/2005 | Funahashi et al. |
| 2005/0224083 A1 | 10/2005 | Crass |
| 2005/0234746 A1 | 10/2005 | Funahashi |
| 2005/0240305 A1 | 10/2005 | Bogash et al. |
| 2005/0246416 A1 | 11/2005 | Blomquist |
| 2005/0251418 A1 | 11/2005 | Fox, Jr. et al. |
| 2005/0261660 A1 | 11/2005 | Choi |
| 2005/0273059 A1 | 12/2005 | Mernoe et al. |
| 2005/0273367 A1 | 12/2005 | Nourie et al. |
| 2005/0277873 A1 | 12/2005 | Stewart et al. |
| 2005/0277890 A1 | 12/2005 | Stewart et al. |
| 2005/0277911 A1 | 12/2005 | Stewart et al. |
| 2005/0278194 A1 | 12/2005 | Holland et al. |
| 2006/0004772 A1 | 1/2006 | Hagan et al. |
| 2006/0009727 A1 | 1/2006 | O'Mahony et al. |
| 2006/0009734 A1 | 1/2006 | Martin |
| 2006/0010098 A1 | 1/2006 | Goodnow et al. |
| 2006/0042139 A1 | 3/2006 | Mendes |
| 2006/0047270 A1 | 3/2006 | Shelton |
| 2006/0047538 A1* | 3/2006 | Condurso ............. G06F 19/326 705/3 |
| 2006/0053036 A1 | 3/2006 | Coffman et al. |
| 2006/0064020 A1 | 3/2006 | Burnes et al. |
| 2006/0074633 A1 | 4/2006 | Mahesh et al. |
| 2006/0074920 A1 | 4/2006 | Wefers et al. |

(56) References Cited

U.S. PATENT DOCUMENTS

| | | |
|---|---|---|
| 2006/0079831 A1 | 4/2006 | Gilbert |
| 2006/0089854 A1 | 4/2006 | Holland et al. |
| 2006/0089855 A1 | 4/2006 | Holland et al. |
| 2006/0100746 A1 | 5/2006 | Leibner-Druska |
| 2006/0100907 A1 | 5/2006 | Holland et al. |
| 2006/0106649 A1 | 5/2006 | Eggers et al. |
| 2006/0111943 A1 | 5/2006 | Wu |
| 2006/0116904 A1 | 6/2006 | Brem |
| 2006/0116907 A1 | 6/2006 | Rhodes et al. |
| 2006/0122481 A1 | 6/2006 | Sievenpiper et al. |
| 2006/0122867 A1 | 6/2006 | Eggers et al. |
| 2006/0129140 A1 | 6/2006 | Todd et al. |
| 2006/0129429 A1 | 6/2006 | Moubayed et al. |
| 2006/0129434 A1 | 6/2006 | Smitherman et al. |
| 2006/0129435 A1 | 6/2006 | Smitherman et al. |
| 2006/0136266 A1 | 6/2006 | Tarassenko et al. |
| 2006/0136271 A1 | 6/2006 | Eggers et al. |
| 2006/0143051 A1 | 6/2006 | Eggers et al. |
| 2006/0173260 A1 | 8/2006 | Gaoni et al. |
| 2006/0173406 A1 | 8/2006 | Hayes et al. |
| 2006/0173715 A1 | 8/2006 | Wang et al. |
| 2006/0173927 A1 | 8/2006 | Beyer et al. |
| 2006/0190302 A1 | 8/2006 | Eggers et al. |
| 2006/0195022 A1 | 8/2006 | Trepagnier et al. |
| 2006/0200007 A1 | 9/2006 | Brockway et al. |
| 2006/0200369 A1 | 9/2006 | Batch et al. |
| 2006/0211404 A1 | 9/2006 | Cromp et al. |
| 2006/0224141 A1 | 10/2006 | Rush et al. |
| 2006/0229918 A1 | 10/2006 | Fotsch et al. |
| 2006/0247606 A1 | 11/2006 | Batch |
| 2006/0258985 A1 | 11/2006 | Russell |
| 2006/0259327 A1 | 11/2006 | Hoag |
| 2006/0264895 A1 | 11/2006 | Flanders |
| 2006/0265246 A1 | 11/2006 | Hoag |
| 2006/0267753 A1 | 11/2006 | Hussey et al. |
| 2006/0268710 A1 | 11/2006 | Appanna et al. |
| 2006/0270971 A1 | 11/2006 | Gelfand et al. |
| 2006/0277206 A1 | 12/2006 | Bailey et al. |
| 2006/0287885 A1 | 12/2006 | Frick |
| 2007/0015972 A1 | 1/2007 | Wang et al. |
| 2007/0016443 A1 | 1/2007 | Wachman et al. |
| 2007/0021715 A1 | 1/2007 | Kohlbrenner et al. |
| 2007/0027506 A1 | 2/2007 | Stender et al. |
| 2007/0060796 A1 | 3/2007 | Kim |
| 2007/0060870 A1 | 3/2007 | Tolle et al. |
| 2007/0060871 A1 | 3/2007 | Istoc |
| 2007/0061393 A1 | 3/2007 | Moore |
| 2007/0065363 A1 | 3/2007 | Dalal et al. |
| 2007/0073419 A1 | 3/2007 | Sesay |
| 2007/0078314 A1 | 4/2007 | Grounsell |
| 2007/0083870 A1 | 4/2007 | Kanakogi |
| 2007/0088333 A1 | 4/2007 | Levin et al. |
| 2007/0093786 A1 | 4/2007 | Goldsmith et al. |
| 2007/0100665 A1 | 5/2007 | Brown |
| 2007/0100667 A1 | 5/2007 | Bardy |
| 2007/0106126 A1 | 5/2007 | Mannheimer et al. |
| 2007/0112298 A1 | 5/2007 | Mueller et al. |
| 2007/0116037 A1 | 5/2007 | Moore |
| 2007/0118405 A1 | 5/2007 | Campbell et al. |
| 2007/0135866 A1 | 6/2007 | Baker et al. |
| 2007/0136098 A1 | 6/2007 | Smythe et al. |
| 2007/0142822 A1 | 6/2007 | Remde |
| 2007/0156282 A1 | 7/2007 | Dunn |
| 2007/0156452 A1 | 7/2007 | Batch |
| 2007/0169008 A1 | 7/2007 | Varanasi et al. |
| 2007/0179448 A1 | 8/2007 | Lim et al. |
| 2007/0186923 A1 | 8/2007 | Poutiatine et al. |
| 2007/0191817 A1 | 8/2007 | Martin |
| 2007/0191973 A1 | 8/2007 | Holzbauer et al. |
| 2007/0213657 A1 | 9/2007 | Jennewine et al. |
| 2007/0213684 A1 | 9/2007 | Hickle et al. |
| 2007/0214003 A1 | 9/2007 | Holland et al. |
| 2007/0215545 A1 | 9/2007 | Bissler et al. |
| 2007/0229249 A1 | 10/2007 | McNeal et al. |
| 2007/0232867 A1 | 10/2007 | Hansmann |
| 2007/0233035 A1 | 10/2007 | Wehba et al. |
| 2007/0233049 A1 | 10/2007 | Wehba et al. |
| 2007/0233206 A1 | 10/2007 | Frikart |
| 2007/0233520 A1 | 10/2007 | Wehba et al. |
| 2007/0251835 A1 | 11/2007 | Mehta et al. |
| 2007/0253021 A1 | 11/2007 | Mehta et al. |
| 2007/0254593 A1 | 11/2007 | Jollota et al. |
| 2007/0255125 A1 | 11/2007 | Moberg et al. |
| 2007/0257788 A1 | 11/2007 | Carlson |
| 2007/0258395 A1 | 11/2007 | Jollota et al. |
| 2007/0299389 A1 | 12/2007 | Halbert et al. |
| 2007/0299687 A1 | 12/2007 | Palmer et al. |
| 2007/0299695 A1 | 12/2007 | Jung et al. |
| 2008/0001771 A1 | 1/2008 | Faoro et al. |
| 2008/0004904 A1 | 1/2008 | Tran |
| 2008/0009684 A1 | 1/2008 | Corsetti et al. |
| 2008/0033361 A1 | 2/2008 | Evans et al. |
| 2008/0033966 A1 | 2/2008 | Wahl |
| 2008/0034323 A1 | 2/2008 | Blomquist |
| 2008/0041942 A1 | 2/2008 | Aissa |
| 2008/0052704 A1 | 2/2008 | Wysocki |
| 2008/0065007 A1 | 3/2008 | Peterson et al. |
| 2008/0065417 A1 | 3/2008 | Jung et al. |
| 2008/0071217 A1 | 3/2008 | Moubayed et al. |
| 2008/0071251 A1 | 3/2008 | Moubayed et al. |
| 2008/0091466 A1 | 4/2008 | Butler et al. |
| 2008/0095339 A1 | 4/2008 | Elliott |
| 2008/0097289 A1 | 4/2008 | Steil et al. |
| 2008/0097552 A1 | 4/2008 | Dicks et al. |
| 2008/0126969 A1 | 5/2008 | Blomquist |
| 2008/0139907 A1 | 6/2008 | Rao et al. |
| 2008/0148047 A1 | 6/2008 | Appenzeller et al. |
| 2008/0149117 A1 | 6/2008 | Raghuram |
| 2008/0154177 A1 | 6/2008 | Moubayed et al. |
| 2008/0172337 A1 | 7/2008 | Banfield et al. |
| 2008/0184219 A1 | 7/2008 | Matsumoto |
| 2008/0188796 A1 | 8/2008 | Steil et al. |
| 2008/0200870 A1 | 8/2008 | Palmroos et al. |
| 2008/0214919 A1 | 9/2008 | Harmon et al. |
| 2008/0243055 A1 | 10/2008 | Fathallah et al. |
| 2008/0246748 A1 | 10/2008 | Cassidy et al. |
| 2008/0256305 A1 | 10/2008 | Kwon |
| 2008/0259926 A1 | 10/2008 | Tavares et al. |
| 2008/0262469 A1 | 10/2008 | Bristol et al. |
| 2008/0269714 A1 | 10/2008 | Mastrototaro et al. |
| 2008/0269723 A1 | 10/2008 | Mastrototaro et al. |
| 2008/0275384 A1 | 11/2008 | Mastrototaro et al. |
| 2008/0300572 A1 | 12/2008 | Rankers et al. |
| 2008/0301298 A1 | 12/2008 | Bernardi et al. |
| 2008/0320387 A1 | 12/2008 | Sasaki et al. |
| 2008/0320466 A1 | 12/2008 | Dias |
| 2009/0003554 A1 | 1/2009 | Katis et al. |
| 2009/0005703 A1 | 1/2009 | Fasciano |
| 2009/0005728 A1 | 1/2009 | Weinert et al. |
| 2009/0006061 A1 | 1/2009 | Thukral et al. |
| 2009/0006129 A1 | 1/2009 | Thukral |
| 2009/0006133 A1 | 1/2009 | Weinert |
| 2009/0018495 A1 | 1/2009 | Panduro |
| 2009/0036750 A1 | 2/2009 | Weinstein et al. |
| 2009/0051560 A1 | 2/2009 | Manning et al. |
| 2009/0054743 A1 | 2/2009 | Stewart |
| 2009/0054754 A1 | 2/2009 | McMahon et al. |
| 2009/0057399 A1 | 3/2009 | Sajkowsky |
| 2009/0063187 A1 | 3/2009 | Johnson et al. |
| 2009/0069785 A1 | 3/2009 | Miller et al. |
| 2009/0099867 A1 | 4/2009 | Newman |
| 2009/0135196 A1 | 5/2009 | Holland et al. |
| 2009/0143662 A1 | 6/2009 | Estes et al. |
| 2009/0149743 A1 | 6/2009 | Barron et al. |
| 2009/0150174 A1 | 6/2009 | Buck et al. |
| 2009/0150439 A1 | 6/2009 | Gejdos et al. |
| 2009/0150878 A1 | 6/2009 | Pathak et al. |
| 2009/0156991 A1 | 6/2009 | Roberts |
| 2009/0157695 A1 | 6/2009 | Roberts |
| 2009/0158274 A1 | 6/2009 | Roberts |
| 2009/0177146 A1 | 7/2009 | Nesbitt et al. |
| 2009/0177769 A1 | 7/2009 | Roberts |
| 2009/0177992 A1 | 7/2009 | Rubalcaba et al. |
| 2009/0183147 A1 | 7/2009 | Davis et al. |

(56) References Cited

U.S. PATENT DOCUMENTS

| | | |
|---|---|---|
| 2009/0209938 A1 | 8/2009 | Aalto-Setala |
| 2009/0210250 A1 | 8/2009 | Prax et al. |
| 2009/0221890 A1 | 9/2009 | Saffer et al. |
| 2009/0231249 A1 | 9/2009 | Wang et al. |
| 2009/0270833 A1 | 10/2009 | DeBelser |
| 2009/0275886 A1 | 11/2009 | Blomquist et al. |
| 2009/0275896 A1 | 11/2009 | Kamen et al. |
| 2009/0284691 A1 | 11/2009 | Marhefka et al. |
| 2009/0292340 A1 | 11/2009 | Mass et al. |
| 2009/0306573 A1 | 12/2009 | Gagner et al. |
| 2009/0326340 A1 | 12/2009 | Wang |
| 2009/0326516 A1 | 12/2009 | Bangera et al. |
| 2010/0008377 A1 | 1/2010 | Hasti et al. |
| 2010/0022988 A1 | 1/2010 | Wochner |
| 2010/0036310 A1 | 2/2010 | Hillman |
| 2010/0056992 A1 | 3/2010 | Hayter |
| 2010/0083060 A1 | 4/2010 | Rahman |
| 2010/0095229 A1 | 4/2010 | Dixon et al. |
| 2010/0121170 A1 | 5/2010 | Rule |
| 2010/0121246 A1 | 5/2010 | Peters et al. |
| 2010/0121415 A1 | 5/2010 | Skelton et al. |
| 2010/0121654 A1 | 5/2010 | Portnoy et al. |
| 2010/0121752 A1 | 5/2010 | Banigan et al. |
| 2010/0130933 A1 | 5/2010 | Holland et al. |
| 2010/0131434 A1 | 5/2010 | Magent et al. |
| 2010/0138523 A1 | 6/2010 | Umess et al. |
| 2010/0146137 A1 | 6/2010 | Wu et al. |
| 2010/0156633 A1 | 6/2010 | Buck et al. |
| 2010/0160854 A1 | 6/2010 | Gauthier |
| 2010/0160860 A1 | 6/2010 | Celentano et al. |
| 2010/0174266 A1 | 7/2010 | Estes |
| 2010/0191525 A1 | 7/2010 | Rabenko et al. |
| 2010/0198034 A1 | 8/2010 | Thomas et al. |
| 2010/0198196 A1 | 8/2010 | Wei |
| 2010/0200506 A1 | 8/2010 | Ware et al. |
| 2010/0209268 A1 | 8/2010 | Davis |
| 2010/0212675 A1 | 8/2010 | Walling et al. |
| 2010/0217621 A1 | 8/2010 | Schoenberg |
| 2010/0234708 A1 | 9/2010 | Buck et al. |
| 2010/0250732 A1 | 9/2010 | Bucknell |
| 2010/0268157 A1 | 10/2010 | Wehba et al. |
| 2010/0271479 A1 | 10/2010 | Heydlauf |
| 2010/0273738 A1 | 10/2010 | Valcke et al. |
| 2010/0274218 A1 | 10/2010 | Yodfat et al. |
| 2010/0280486 A1 | 11/2010 | Khair et al. |
| 2010/0292634 A1 | 11/2010 | Kircher |
| 2010/0298765 A1 | 11/2010 | Budiman et al. |
| 2010/0318025 A1 | 12/2010 | John |
| 2011/0001605 A1 | 1/2011 | Kiani et al. |
| 2011/0021898 A1 | 1/2011 | Wei et al. |
| 2011/0028885 A1 | 2/2011 | Eggers et al. |
| 2011/0040158 A1 | 2/2011 | Katz et al. |
| 2011/0060758 A1 | 3/2011 | Schlotterbeck et al. |
| 2011/0071844 A1 | 3/2011 | Cannon et al. |
| 2011/0072379 A1 | 3/2011 | Gannon |
| 2011/0078253 A1 | 3/2011 | Chan et al. |
| 2011/0078608 A1 | 3/2011 | Gannon et al. |
| 2011/0093284 A1 | 4/2011 | Dicks et al. |
| 2011/0099313 A1 | 4/2011 | Bolanowski |
| 2011/0125095 A1 | 5/2011 | Lebel et al. |
| 2011/0138185 A1 | 6/2011 | Ju et al. |
| 2011/0166628 A1 | 7/2011 | Jain |
| 2011/0175728 A1 | 7/2011 | Baker, Jr. |
| 2011/0178462 A1 | 7/2011 | Moberg et al. |
| 2011/0185010 A1 | 7/2011 | Shatsky et al. |
| 2011/0196748 A1 | 8/2011 | Caron et al. |
| 2011/0231216 A1 | 9/2011 | Fyke et al. |
| 2011/0257496 A1 | 10/2011 | Terashima et al. |
| 2011/0257798 A1 | 10/2011 | Ali et al. |
| 2011/0259954 A1 | 10/2011 | Bartz et al. |
| 2011/0264043 A1 | 10/2011 | Kotnick et al. |
| 2011/0264044 A1 | 10/2011 | Bartz et al. |
| 2011/0266221 A1 | 11/2011 | Ware et al. |
| 2011/0270045 A1 | 11/2011 | Lebel et al. |
| 2011/0275904 A1 | 11/2011 | Lebel et al. |
| 2011/0286457 A1 | 11/2011 | Ee |
| 2011/0289314 A1 | 11/2011 | Whitcomb |
| 2011/0289497 A1 | 11/2011 | Kiaie et al. |
| 2011/0295196 A1 | 12/2011 | Chazot et al. |
| 2011/0295341 A1 | 12/2011 | Estes et al. |
| 2011/0296051 A1 | 12/2011 | Vange |
| 2011/0296411 A1 | 12/2011 | Tang et al. |
| 2011/0313789 A1 | 12/2011 | Karmen et al. |
| 2011/0319813 A1 | 12/2011 | Kamen et al. |
| 2011/0320049 A1 | 12/2011 | Chossat et al. |
| 2012/0005680 A1 | 1/2012 | Dolby et al. |
| 2012/0011253 A1 | 1/2012 | Friedman et al. |
| 2012/0016305 A1 | 1/2012 | Jollota |
| 2012/0029941 A1 | 2/2012 | Malave et al. |
| 2012/0036102 A1 | 2/2012 | Fletcher et al. |
| 2012/0066501 A1 | 3/2012 | Xiong |
| 2012/0070045 A1 | 3/2012 | Vesper et al. |
| 2012/0095437 A1 | 4/2012 | Hemmerling |
| 2012/0112903 A1 | 5/2012 | Kaib et al. |
| 2012/0130198 A1 | 5/2012 | Beaule |
| 2012/0130308 A1 | 5/2012 | Silkaitis et al. |
| 2012/0143116 A1 | 6/2012 | Ware et al. |
| 2012/0150556 A1 | 6/2012 | Galasso et al. |
| 2012/0157920 A1 | 6/2012 | Flachbart et al. |
| 2012/0172802 A1 | 7/2012 | Blomquist et al. |
| 2012/0179135 A1 | 7/2012 | Rinehart et al. |
| 2012/0179136 A1 | 7/2012 | Rinehart et al. |
| 2012/0185267 A1 | 7/2012 | Kamen et al. |
| 2012/0203177 A1 | 8/2012 | Lanier |
| 2012/0245554 A1 | 9/2012 | Kawamura |
| 2012/0259978 A1 | 10/2012 | Petersen et al. |
| 2012/0260012 A1 | 10/2012 | Gao-Saari et al. |
| 2012/0277716 A1 | 11/2012 | Ali et al. |
| 2012/0283630 A1 | 11/2012 | Lee et al. |
| 2012/0284734 A1 | 11/2012 | McQuaid et al. |
| 2012/0323212 A1 | 12/2012 | Murphy |
| 2012/0330380 A1 | 12/2012 | Corndorf |
| 2013/0006666 A1 | 1/2013 | Schneider |
| 2013/0006702 A1 | 1/2013 | Wu |
| 2013/0012877 A1 | 1/2013 | Debelser et al. |
| 2013/0012879 A1 | 1/2013 | Debelser et al. |
| 2013/0012880 A1 | 1/2013 | Blomquist |
| 2013/0015980 A1 | 1/2013 | Evans et al. |
| 2013/0036403 A1 | 2/2013 | Geist |
| 2013/0036412 A1 | 2/2013 | Birtwhistle et al. |
| 2013/0066265 A1 | 3/2013 | Grant |
| 2013/0072872 A1 | 3/2013 | Yodfat et al. |
| 2013/0085689 A1 | 4/2013 | Sur et al. |
| 2013/0096444 A1 | 4/2013 | Condurso et al. |
| 2013/0096648 A1 | 4/2013 | Benson |
| 2013/0102963 A1 | 4/2013 | Marsh et al. |
| 2013/0114594 A1 | 5/2013 | Van Zijst |
| 2013/0138452 A1 | 5/2013 | Cork et al. |
| 2013/0144206 A1 | 6/2013 | Lee et al. |
| 2013/0150824 A1 | 6/2013 | Estes et al. |
| 2013/0158504 A1 | 6/2013 | Ruchti et al. |
| 2013/0167245 A1 | 6/2013 | Birtwhistle et al. |
| 2013/0173473 A1 | 7/2013 | Birtwhistle et al. |
| 2013/0191770 A1 | 7/2013 | Bartz et al. |
| 2013/0204188 A1 | 8/2013 | Kamen et al. |
| 2013/0218080 A1 | 8/2013 | Peterfreund et al. |
| 2013/0261993 A1 | 10/2013 | Ruchti et al. |
| 2013/0274669 A1 | 10/2013 | Stempfle et al. |
| 2013/0275539 A1 | 10/2013 | Gross et al. |
| 2013/0291116 A1 | 10/2013 | Homer |
| 2013/0296823 A1 | 11/2013 | Melker et al. |
| 2013/0296984 A1 | 11/2013 | Burnett et al. |
| 2013/0317753 A1 | 11/2013 | Kamen et al. |
| 2013/0346108 A1 | 12/2013 | Kamen et al. |
| 2014/0025392 A1 | 1/2014 | Chandrasenan |
| 2014/0039446 A1 | 2/2014 | Day |
| 2014/0142963 A1 | 5/2014 | Hill et al. |
| 2014/0163517 A1 | 6/2014 | Finan et al. |
| 2014/0180711 A1 | 6/2014 | Kamen et al. |
| 2014/0197950 A1 | 7/2014 | Shupp et al. |
| 2014/0215490 A1 | 7/2014 | Mathur et al. |
| 2014/0257251 A1 | 9/2014 | Bush et al. |
| 2014/0266790 A1 | 9/2014 | Al-Ali et al. |
| 2014/0266794 A1 | 9/2014 | Brown et al. |

(56) References Cited

U.S. PATENT DOCUMENTS

| | | |
|---|---|---|
| 2014/0269643 A1 | 9/2014 | Sun |
| 2014/0276571 A1 | 9/2014 | Ludolph |
| 2014/0280522 A1 | 9/2014 | Watte |
| 2014/0288947 A1 | 9/2014 | Simpson et al. |
| 2014/0294177 A1 | 10/2014 | Shastry et al. |
| 2014/0297329 A1 | 10/2014 | Rock |
| 2014/0316819 A1 | 10/2014 | Dunsirn et al. |
| 2014/0318639 A1 | 10/2014 | Peret et al. |
| 2014/0350513 A1 | 11/2014 | Oruklu et al. |
| 2014/0358077 A1 | 12/2014 | Oruklu et al. |
| 2014/0366878 A1 | 12/2014 | Baron |
| 2015/0005935 A1 | 1/2015 | Bae et al. |
| 2015/0006907 A1 | 1/2015 | Brouwer et al. |
| 2015/0045729 A1 | 2/2015 | Denzer et al. |
| 2015/0058044 A1 | 2/2015 | Butler et al. |
| 2015/0058960 A1 | 2/2015 | Schmoyer et al. |
| 2015/0066531 A1 | 3/2015 | Jacobson et al. |
| 2015/0100038 A1 | 4/2015 | McCann et al. |
| 2015/0100787 A1 | 4/2015 | Westin et al. |
| 2015/0117234 A1 | 4/2015 | Raman et al. |
| 2015/0134265 A1 | 5/2015 | Kohlbrecher et al. |
| 2015/0141955 A1 | 5/2015 | Ruchti et al. |
| 2015/0151051 A1 | 6/2015 | Tsoukalis |
| 2015/0161354 A1 | 6/2015 | Blomquist |
| 2015/0199192 A1 | 7/2015 | Borges et al. |
| 2015/0230760 A1 | 8/2015 | Schneider |
| 2015/0281128 A1 | 10/2015 | Sindhu |
| 2015/0328396 A1 | 11/2015 | Adams et al. |
| 2015/0371004 A1 | 12/2015 | Jones |
| 2015/0379237 A1 | 12/2015 | Mills et al. |
| 2016/0006695 A1 | 1/2016 | Prodoehl et al. |
| 2016/0015885 A1 | 1/2016 | Pananen et al. |
| 2016/0034655 A1 | 2/2016 | Gray et al. |
| 2016/0045661 A1 | 2/2016 | Gray et al. |
| 2016/0051749 A1 | 2/2016 | Istoc |
| 2016/0051751 A1 | 2/2016 | Silkaitis et al. |
| 2016/0063471 A1 | 3/2016 | Kobres et al. |
| 2016/0103960 A1 | 4/2016 | Hume et al. |
| 2016/0228633 A1 | 8/2016 | Welsch et al. |
| 2016/0241391 A1 | 8/2016 | Fenster |
| 2016/0277152 A1 | 9/2016 | Xiang et al. |
| 2016/0285876 A1 | 9/2016 | Perez et al. |
| 2016/0317742 A1 | 11/2016 | Gannon et al. |
| 2016/0350513 A1 | 12/2016 | Jacobson et al. |
| 2017/0024534 A1 | 1/2017 | Arrizza et al. |
| 2017/0034277 A1 | 2/2017 | Jackson et al. |
| 2017/0063559 A1 | 3/2017 | Wallrabenstein |
| 2017/0099148 A1 | 4/2017 | Ochmanski et al. |
| 2017/0104645 A1 | 4/2017 | Wooton et al. |
| 2017/0111301 A1 | 4/2017 | Robinson |
| 2017/0147761 A1 | 5/2017 | Moskal et al. |
| 2017/0149567 A1 | 5/2017 | Moskal |
| 2017/0214762 A1 | 7/2017 | Swain et al. |
| 2017/0246388 A1 | 8/2017 | Kohlbrecher |
| 2017/0258401 A1 | 9/2017 | Volpe |
| 2017/0262590 A1 | 9/2017 | Karakosta et al. |
| 2017/0274140 A1 | 9/2017 | Howard et al. |
| 2017/0286637 A1 | 10/2017 | Arrizza et al. |
| 2017/0319780 A1 | 11/2017 | Belkin et al. |
| 2017/0325091 A1 | 11/2017 | Freeman et al. |
| 2017/0331735 A1 | 11/2017 | Jha et al. |
| 2017/0351841 A1 | 12/2017 | Moskal |
| 2018/0028742 A1 | 2/2018 | Day et al. |
| 2018/0043094 A1 | 2/2018 | Day et al. |
| 2018/0063724 A1 | 3/2018 | Zhang et al. |
| 2018/0121613 A1 | 5/2018 | Connely, IV et al. |
| 2018/0126067 A1 | 5/2018 | Ledford et al. |
| 2018/0181712 A1 | 6/2018 | Ensey et al. |
| 2018/0247712 A1 | 8/2018 | Muhsin et al. |
| 2018/0317826 A1 | 11/2018 | Muhsin et al. |
| 2018/0322948 A1 | 11/2018 | Drost et al. |
| 2018/0359085 A1 | 12/2018 | Dervyn |
| 2019/0006044 A1 | 1/2019 | Brask |
| 2019/0036688 A1 | 1/2019 | Wasily et al. |
| 2019/0096518 A1 | 3/2019 | Pace |
| 2019/0132196 A1 | 5/2019 | Trivedi et al. |
| 2019/0147998 A1 | 5/2019 | Ruchti et al. |
| 2019/0166501 A1 | 5/2019 | Debates et al. |
| 2019/0172590 A1 | 6/2019 | Vesto et al. |
| 2019/0228863 A1 | 7/2019 | Dharwad et al. |
| 2019/0229982 A1 | 7/2019 | Ikuta et al. |
| 2019/0243829 A1 | 8/2019 | Butler et al. |
| 2019/0244689 A1 | 8/2019 | Atkin |
| 2019/0245942 A1 | 8/2019 | Moskal |
| 2019/0311803 A1 | 10/2019 | Kohlbrecher et al. |
| 2019/0348160 A1 | 11/2019 | Heavelyn et al. |
| 2019/0392929 A1 | 12/2019 | Gassman |
| 2020/0023127 A1 | 1/2020 | Simpson et al. |
| 2020/0027541 A1 | 1/2020 | Xavier et al. |
| 2020/0027548 A1 | 1/2020 | Xavier et al. |
| 2020/0027549 A1 | 1/2020 | Xavier et al. |
| 2020/0027550 A1 | 1/2020 | Xavier et al. |
| 2020/0027551 A1 | 1/2020 | Xavier et al. |
| 2020/0028837 A1 | 1/2020 | Xavier et al. |
| 2020/0035355 A1 | 1/2020 | Xavier et al. |
| 2020/0054825 A1 | 2/2020 | Kamen et al. |
| 2020/0153627 A1 | 5/2020 | Wentz |
| 2020/0206413 A1 | 7/2020 | Silkaitis et al. |
| 2020/0220865 A1 | 7/2020 | Finger et al. |
| 2020/0282139 A1 | 9/2020 | Susi |
| 2020/0306443 A1 | 10/2020 | Day |
| 2020/0330685 A1 | 10/2020 | Day |
| 2020/0334497 A1 | 10/2020 | Barrett et al. |
| 2020/0335194 A1 | 10/2020 | Jacobson et al. |
| 2020/0351376 A1 | 11/2020 | Moskal |
| 2020/0353167 A1 | 11/2020 | Vivek et al. |
| 2020/0353168 A1 | 11/2020 | Keenan et al. |
| 2021/0014259 A1 | 1/2021 | Harris et al. |
| 2021/0043296 A1 | 2/2021 | Xavier et al. |
| 2021/0045640 A1 | 2/2021 | Poltorak |
| 2021/0050097 A1 | 2/2021 | Xavier et al. |
| 2021/0085855 A1 | 3/2021 | Belkin et al. |
| 2021/0098106 A1 | 4/2021 | Kohlbrecher et al. |
| 2021/0098107 A1 | 4/2021 | Xavier et al. |
| 2021/0105206 A1 | 4/2021 | Jha et al. |
| 2021/0375421 A1 | 12/2021 | Ruchti et al. |
| 2021/0375438 A1 | 12/2021 | Xavier et al. |
| 2021/0409362 A1 | 12/2021 | Katis et al. |
| 2022/0037011 A1 | 2/2022 | Fryman |
| 2022/0037012 A1 | 2/2022 | Fryman |
| 2022/0051777 A1 | 2/2022 | Xavier et al. |
| 2022/0062541 A1 | 3/2022 | Kamen et al. |
| 2022/0129452 A1 | 4/2022 | Butler et al. |
| 2022/0139536 A1 | 5/2022 | Xavier et al. |
| 2022/0139537 A1 | 5/2022 | Xavier et al. |
| 2022/0150307 A1 | 5/2022 | Walsh et al. |
| 2022/0165404 A1 | 5/2022 | Vivek et al. |
| 2022/0189605 A1 | 6/2022 | Kelly et al. |
| 2022/0223283 A1 | 7/2022 | Biasi et al. |
| 2022/0328175 A1 | 10/2022 | Arrizza et al. |
| 2022/0331513 A1 | 10/2022 | Howard et al. |
| 2022/0344023 A1 | 10/2022 | Xavier et al. |
| 2022/0375565 A1 | 11/2022 | Xavier et al. |
| 2022/0384059 A1 | 12/2022 | Xavier et al. |
| 2023/0009405 A1 | 1/2023 | Xavier et al. |
| 2023/0009417 A1 | 1/2023 | Xavier et al. |
| 2023/0139360 A1 | 5/2023 | Kohlbrecher et al. |
| 2023/0145267 A1 | 5/2023 | Xavier et al. |
| 2023/0147762 A1 | 5/2023 | Xavier et al. |

FOREIGN PATENT DOCUMENTS

| | | |
|---|---|---|
| CA | 2 898 825 | 7/2014 |
| DE | 31 12 762 | 1/1983 |
| DE | 34 35 647 | 7/1985 |
| DE | 198 44 252 | 3/2000 |
| DE | 199 32 147 | 1/2001 |
| DE | 103 52 456 | 7/2005 |
| EP | 0 319 267 | 6/1989 |
| EP | 0 380 061 | 8/1990 |
| EP | 0 384 155 | 8/1990 |
| EP | 0 460 533 | 12/1991 |
| EP | 0 564 127 | 6/1993 |
| EP | 0 633 035 | 1/1995 |

(56) References Cited

FOREIGN PATENT DOCUMENTS

| | | |
|---|---|---|
| EP | 0 652 528 | 5/1995 |
| EP | 0 672 427 | 9/1995 |
| EP | 0 683 465 | 11/1995 |
| EP | 0 880 936 | 12/1998 |
| EP | 1 157 711 | 11/2001 |
| EP | 1 174 817 | 1/2002 |
| EP | 0 664 102 | 4/2002 |
| EP | 1 197 178 | 4/2002 |
| EP | 0 830 775 | 8/2002 |
| EP | 1 500 025 | 4/2003 |
| EP | 2 113 842 | 11/2009 |
| EP | 2 228 004 | 9/2010 |
| EP | 2 243 506 | 10/2010 |
| EP | 2 410 448 | 1/2012 |
| EP | 2 742 961 | 6/2014 |
| EP | 2 874 087 | 5/2015 |
| FR | 2 717 919 | 9/1995 |
| GB | 2 285 135 | 6/1995 |
| JP | 04-161139 | 6/1992 |
| JP | 07-502678 | 3/1995 |
| JP | 11-500643 | 1/1999 |
| JP | 2000-316820 | 11/2000 |
| JP | 2002-531154 | 9/2002 |
| JP | 2003-016183 | 1/2003 |
| JP | 2003-296173 | 10/2003 |
| JP | 2005-021463 | 1/2005 |
| JP | 2005-527284 | 9/2005 |
| JP | 2005-284846 | 10/2005 |
| JP | 2006-047319 | 2/2006 |
| JP | 2006-520949 | 9/2006 |
| JP | 2007-518479 | 7/2007 |
| JP | 2007-525256 | 9/2007 |
| JP | 2008-080036 | 4/2008 |
| JP | 2008-516303 | 5/2008 |
| JP | 2008-158622 | 7/2008 |
| JP | 2008-529675 | 8/2008 |
| JP | 2009-163534 | 7/2009 |
| JP | 2010-502361 | 1/2010 |
| JP | 2011-506048 | 3/2011 |
| JP | 2012-011204 | 1/2012 |
| JP | 2012-070991 | 4/2012 |
| JP | 2012-523895 | 10/2012 |
| JP | 2014-068283 | 4/2014 |
| TW | 200426656 | 12/2004 |
| WO | WO 84/001719 | 5/1984 |
| WO | WO 91/016416 | 10/1991 |
| WO | WO 92/010985 | 7/1992 |
| WO | WO 92/013322 | 8/1992 |
| WO | WO 94/005355 | 3/1994 |
| WO | WO 96/008755 | 3/1996 |
| WO | WO 96/025186 | 8/1996 |
| WO | WO 96/025963 | 8/1996 |
| WO | WO 98/012670 | 3/1998 |
| WO | WO 98/019263 | 5/1998 |
| WO | WO 99/051003 | 10/1999 |
| WO | WO 00/013580 | 3/2000 |
| WO | WO 00/053243 | 9/2000 |
| WO | WO 01/014974 | 3/2001 |
| WO | WO 01/033484 | 5/2001 |
| WO | WO 01/045014 | 6/2001 |
| WO | WO 02/005702 | 1/2002 |
| WO | WO 02/036044 | 5/2002 |
| WO | WO 02/049153 | 6/2002 |
| WO | WO 02/049279 | 6/2002 |
| WO | WO 02/069099 | 9/2002 |
| WO | WO 02/081015 | 10/2002 |
| WO | WO 02/088875 | 11/2002 |
| WO | WO 03/006091 | 1/2003 |
| WO | WO 03/050917 | 6/2003 |
| WO | WO 03/091836 | 11/2003 |
| WO | WO 03/094092 | 11/2003 |
| WO | WO 2004/060455 | 7/2004 |
| WO | WO 2004/070557 | 8/2004 |
| WO | WO 2004/070562 | 8/2004 |
| WO | WO 2004/072828 | 8/2004 |
| WO | WO 2005/036447 | 4/2005 |
| WO | WO 2005/050526 | 6/2005 |
| WO | WO 2005/057175 | 6/2005 |
| WO | WO 2005/066872 | 7/2005 |
| WO | WO 2007/087443 | 8/2007 |
| WO | WO 2007/117705 | 10/2007 |
| WO | WO 2007/127879 | 11/2007 |
| WO | WO 2007/127880 | 11/2007 |
| WO | WO 2008/057729 | 5/2008 |
| WO | WO 2008/067245 | 6/2008 |
| WO | WO 2008/082854 | 7/2008 |
| WO | WO 2008/088490 | 7/2008 |
| WO | WO 2008/097316 | 8/2008 |
| WO | WO 2008/103915 | 8/2008 |
| WO | WO 2008/124478 | 10/2008 |
| WO | WO 2008/134146 | 11/2008 |
| WO | WO 2009/016504 | 2/2009 |
| WO | WO 2009/023406 | 2/2009 |
| WO | WO 2009/023407 | 2/2009 |
| WO | WO 2009/023634 | 2/2009 |
| WO | WO 2009/036327 | 3/2009 |
| WO | WO 2009/049252 | 4/2009 |
| WO | WO 2010/017279 | 2/2010 |
| WO | WO 2010/033919 | 3/2010 |
| WO | WO 2010/053703 | 5/2010 |
| WO | WO 2010/075371 | 7/2010 |
| WO | WO 2010/099313 | 9/2010 |
| WO | WO 2010/114929 | 10/2010 |
| WO | WO 2010/119409 | 10/2010 |
| WO | WO 2010/124127 | 10/2010 |
| WO | WO 2010/130992 | 11/2010 |
| WO | WO 2010/135646 | 11/2010 |
| WO | WO 2010/135654 | 11/2010 |
| WO | WO 2010/135686 | 11/2010 |
| WO | WO 2011/005633 | 1/2011 |
| WO | WO 2011/022549 | 2/2011 |
| WO | WO 2012/048833 | 4/2012 |
| WO | WO 2012/049214 | 4/2012 |
| WO | WO 2012/049218 | 4/2012 |
| WO | WO 2012/120078 | 9/2012 |
| WO | WO 2012/140547 | 10/2012 |
| WO | WO 2012/164556 | 12/2012 |
| WO | WO 2012/170942 | 12/2012 |
| WO | WO 2013/045506 | 4/2013 |
| WO | WO 2014/100736 | 6/2014 |
| WO | WO 2014/131729 | 9/2014 |
| WO | WO 2014/131730 | 9/2014 |
| WO | WO 2015/124569 | 8/2015 |
| WO | WO 2016/179389 | 11/2016 |
| WO | WO 2017/176928 | 10/2017 |
| WO | WO 2019/219290 | 11/2019 |
| WO | WO 2020/227403 | 11/2020 |
| WO | WO 2022/006014 | 1/2022 |
| WO | WO 2022/051230 | 3/2022 |

OTHER PUBLICATIONS

Bellare et al., "Security Proofs for Identity-Based Identification and Signature Schemes", Lecture Notes in Computer Science, Jan. 2009, vol. 22, No. 1, pp. 18.

Block, Alexander, "Secret Sharing and 1-11 Threshold Signatures with BLS", Jul. 2, 2018, https://blog.dash.org/secret-sharing-and-threshold-signatures-with-bls-954d1587b5f, in 8 pages.

Doesburg et al., "Improved Usability of a Multi-Infusion Setup Using a Centralized Control Interface: A Task-Based Usability Test", Aug. 11, 2017, PLoS One, vol. 12, No. 8, pp. 10.

Gutwin et al., "Gone But Not Forgotten: Designing for Disconnection in Synchronous Groupware", CSCW 2010, Feb. 6-10, 2010, Savannah, Georgia, USA., pp. 179-188.

Huang et al., "Secure Identity-Based Data Sharing and Profile Matching for Mobile Healthcare Social Networks in Cloud Computing", vol. 6, Jul. 2018, pp. 36584-36594.

Li et al., "Hijacking an Insulin Pump: Security Attacks and Defenses for a Diabetes Therapy System", 2011 IEEE 13th International Conference on e-Health Networking, Applications and Services, 2011, pp. 150-156.

(56) References Cited

OTHER PUBLICATIONS

Michienzi, Kelly, "Managing Drug Library Updates", Pharmacy Purchasing Products, https://www.pppmag.com/article/1061, Feb. 2012, vol. 9, pp. 22-23.
Nojoumian et al., "Social Secret Sharing in Cloud Computing Using a New Trust Function", 2012 Tenth Annual International Conference on Privacy, Security and Trust, pp. 161-167.
"Sigma Spectrum: Operator's Manual", May 15, 2008, pp. 63. <https://usme.com/content/manuals/sigma-spectrum-operator-manual.pdf>.
Solapurkar et al., "Building Secure Healthcare Services Using OAuth 2.0 and JSON Web Token in IOT Cloud Scenario", Dec. 2016, 2nd International Conference on Contemporary Computing and Informatics, pp. 99-10.
"TCG TPM v2.0 Provisioning Guidance", Reference, Version 1, Revision 1, Mar. 15, 2017, pp. 1-43.
Yoo et al., "Code-Based Authentication Scheme for Lightweight Integrity Checking of Smart Vehicles", IEEE Access, 2018, vol. 6, pp. 46731-46741.
Akridge, Jeannie, "New Pumps Outsmart User Error", Healthcare Purchasing News, Apr. 2011, pp. 10, <http://web.archive.org/web/20110426122450/http://www.hpnonline.com/inside/2011-04/1104-OR-Pumps.html>.
Alur et al., "Formal Specifications and Analysis of the Computer-Assisted Resuscitation Algorithm (CARA) Infusion Pump Control System", International Journal on Software Tools for Technology Transfer, Feb. 2004, vol. 5, No. 4, pp. 308-319.
Aragon, Daleen RN, Ph.D., CCRN, "Evaluation of Nursing Work Effort and Perceptions About Blood Glucose Testing in Tight Glycemic Control", American Journal of Critical Care, Jul. 2006, vol. 15, No. 4, pp. 370-377.
ASHP Advantage, "Improving Medication Safety in Health Systems Through Innovations in Automation Technology", Proceedings of Educational Symposium and Educational Sessions during the 39th ASHP Midyear Clinical Meeting, Dec. 5-9, 2004, Orlando, FL, pp. 28.
Beard et al., "Total Quality Pain Management: History, Background, Resources", Abbott Laboratories, TQPM Survey History, available Feb. 2015 or earlier, pp. 1-3.
Bektas et al., "Bluetooth Communication Employing Antenna Diversity", Proceedings of Eight IEEE International Symposium on Computers and Communication, Jul. 2003, pp. 6.
Bequette, Ph.D., "A Critical Assessment of Algorithms and Challenges in the Development of a Closed-Loop Artificial Pancreas", Diabetes Technology & Therapeutics, Feb. 28, 2005, vol. 7, No. 1, pp. 28-47.
Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.
Braun, "Infusomat® Space and Accessories", Instructions for Use, Nov. 2010, pp. 68. <http://corp.bbraun.ee/Extranet/Infusionipumbad/Kasutusjuhendid/Vanad/Kasutusjuhend-Infusomat_Space(vers688J,inglise_k).pdf>.
Brownlee, Seth, "Product Spotlight: The Plum A+ with Hospira MedNet Infusion System", PP&P Magazine, Dec. 2005, vol. 2, No. 7, pp. 2.
Cannon, MD et al., "Automated Heparin-Delivery System to Control Activated Partial Thromboplastin Time", Circulation, Feb. 16, 1999, vol. 99, pp. 751-756.
Cardinal Health, "Alaris® Syringe Pumps" Technical Service Manual, Copyright 2002-2006, Issue 9, pp. 1-88, <http://www.frankshospitalworkshop.com/equipment/documents/infusion_pumps/service_manuals/Cardinal_Alaris_-_Service_Manual.pdf>.
"CareAware® Infusion Management", Cerner Store, as printed May 12, 2011, pp. 3, <https://store.cerner.com/items/7>.
Chen et al., "Enabling Location-Based Services on Wireless LANs", The 11th IEEE International Conference on Networks, ICON 2003, Sep. 28-Oct. 1, 2003, pp. 567-572.
"Computer Dictionary", Microsoft Press, Third Edition, Microsoft Press, 1997, pp. 430 & 506.

"Context-Free Grammar", Wikipedia.org, as last modified Mar. 5, 2010 in 11 pages, <https://en.wikipedia.org/w/index.php/?title=Context-free_grammar&oldid=347915989>.
Crawford, Anne J., MSN, RNC, "Building a Successful Quality Pain Service: Using Patient Satisfaction Data and the Clinical Practice Guideline", USA, 1995, pp. 1-6.
Crocker et al., "Augmented BNF for Syntax Specifications: ABNF", Network Working Group, Standards Track, Jan. 2008, pp. 16.
Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.
Davies, T., "Cordless Data Acquisition in a Hospital Environment", IEE Colloquium on Cordless Computing—Systems and User Experience, 1993, pp. 4.
Dayhoff et al., "Medical Data Capture and Display: The Importance of Clinicians' Workstation Design", AMIA, Inc., 1994, pp. 541-545.
Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.
"Download", Free On-Line Dictionary of Computing, as archived Jun. 16, 2010 in 1 page, http://web.archive.org/web/20100616010314/https://foldoc.org/download.
East PhD et al., "Digital Electronic Communication Between ICU Ventilators and Computers and Printers", Respiratory Care, Sep. 1992, vol. 37, No. 9, pp. 1113-1122.
Edworthy, Judy, "Medical Audible Alarms: A Review", Journal of the American Medical Informatics Association, vol. 20, No. 3, 2013, pp. 584-589.
Einhorn, George W., "Total Quality Pain Management: A Computerized Quality Assessment Tool for Postoperative Pain Management", Abbott Laboratories, Chicago, IL, Mar. 2, 2000, pp. 1-4.
Eskew et al., "Using Innovative Technologies to Set New Safety Standards for the Infusion of Intravenous Medications", Hospital Pharmacy, 2002, vol. 37, No. 11, pp. 1179-1189.
Felleiter et al., "Data Processing in Prehospital Emergency Medicine", International journal of Clinical Monitoring and Computing, Feb. 1995, vol. 12, No. 1, pp. 37-41.
"File Verification", Wikipedia.org, as last modified Oct. 11, 2011 in 2 pages, <https://en.wikipedia.org/w/index.php?title=File_verification&oldid=455048290>.
Fogt et al., Development and Evaluation of a Glucose Analyzer for a Glucose-Controlled Insulin Infusion System (Biostator®), Clinical Chemistry, 1978, vol. 24, No. 8, pp. 1366-1372.
Gabel et al., "Camp: A Common API for Measuring Performance", 21st Large Installations System Administration Conference (LISA '07), 2007, pp. 49-61.
Gage et al., "Automated Anesthesia Surgery Medical Record System", International Journal of Clinical Monitoring and Computing, Dec. 1990, vol. 7, No. 4, pp. 259-263.
Galt et al., "Personal Digital Assistant-Based Drug Information Sources: Potential to Improve Medication Safety", Journal of Medical Library Association, Apr. 2005, vol. 93, No. 2, pp. 229-236.
Gardner, Ph.D et al., "Real Time Data Acquisition: Recommendations for the Medical Information Bus (MIB)", 1992, pp. 813-817.
"General-Purpose Infusion Pumps", Health Devices, EXRI Institute, Oct. 1, 2002, vol. 31, No. 10, pp. 353-387.
Givens et al., "Exploring the Internal State of User Interfaces by Combining Computer Vision Techniques with Grammatical Inference", Proceedings of the 2013 International Conference on Software Engineering, San Francisco, CA, May 18-26, 2013, pp. 1165-1168.
Glaeser, "A Hierarchical Minicomputer System for Continuous Post-Surgical Monitoring", Computers and Biomedical Research, Aug. 31, 1975, pp. 336-361.
Goldberg et al., "Clinical Results of an Updated Insulin Infusion Protocol in Critically Ill Patients", Diabetes Spectrum, 2005, vol. 18, No. 3, pp. 188-191.
Gomez et al., "CLAM: Connection-Less, Lightweight, and Multiway Communication Support for Distributed Computing", Computer Science, 1997, vol. 1199, pp. 227-240.

(56) References Cited

OTHER PUBLICATIONS

"GPS Tracker for Medical Equipment", <http://www.trackingsystem.com/forbusinesses/corporate-trackingsystem/1098-gps-tracker-formedicalequipment.html>, Mar. 15, 2015, pp. 2.
Graseby, "Model 3000/500 and Micro 3100/505: Volumetric Infusion Pump", Technical Service Manual, Graseby Medical Ltd., Apr. 2002, Issue A, pp. 160.
Graseby, "Model 3000/500 and Micro 3100/505: Volumetric Infusion Pump: Illustrated Parts List for Pump Serial Nos. from 3000 to 59,999", Technical Service Manual, Graseby Medical Ltd., Apr. 2002, Issue A, pp. 71.
Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.
Hamann et al., "PUMPSIM: A Software Package for Simulating Computer-Controlled Drug Infusion Pumps", Annual International Conference of the IEEE Engineering in Medicine and Biology Society, 1990, vol. 12, No. 5, pp. 2019-2020.
Hasegawa et al., "On a Portable Memory Device for Physical Activities and Informations of Maternal Perception", Journal of Perinatal Medicine, 1988, vol. 16, No. 4, pp. 349-356.
Hawley et al., "Clinical Implementation of an Automated Medical Information Bus in an Intensive Care Unit", Proceedings of the Annual Symposium on Computer Application in Medical Care, Nov. 9, 1988, pp. 621-624.
Hayes-Roth et al., "Guardian: A Prototype Intelligent Agent for Intensive-Care Monitoring", Artificial Intelligence in Medicine, vol. 4, Dec. 31, 1992, pp. 165-185.
Hospira, GemStar® Pain Management Infusion System 9-084-PR1-2-2, <www.hospira.com/products/gemstar_painmanagement.aspx>, Jan. 28, 2010, pp. 1-2.
Introducing Abbott TQPM (Total Quality Pain Management), Abbott Laboratories, Abbott Park, IL, May 2000, pp. 1-4.
"Infusion Pump", Wikipedia.org, as last modified Mar. 27, 2014, in 3 pages, <https://web.archive.org/web/20140703024932/https://en.wikipedia.org/wiki/Infusion_pump>.
Isaka et al., "Control Strategies for Arterial Blood Pressure Regulation", IEEE Transactions on Biomedical Engineering, Apr. 1993, vol. 40, No. 4, pp. 353-363.
Johnson et al., "Using BCMA Software to Improve Patient Safety In Veterans Administration Medical Centers", Journal of Healthcare Information Management, Dec. 6, 2004, vol. 16, No. 1, pp. 46-51.
Kent Displays, "Reflex™ Electronic Skins", Product Brief 25127B, 2009, pp. 2.
Kent Displays, "Reflex Electronic Skins Engineering Evaluation Kit", 25136A, Mar. 10, 2009.
Lefkowitz et al., "A Trial of the Use of Bar Code Technology to Restructure a Drug Distribution and Administration System", Hospital Pharmacy, Mar. 31, 1991, vol. 26, No. 3, pp. 239-242.
Lenssen et al., "Bright Color Electronic Paper Technology and Applications", IDS '09 Publication EP1-2 (Phillips Research), 2009, pp. 529-532.
Leveson, Nancy, "Medical Devices: The Therac-25", Appendix A, University of Washington, 1995, pp. 49.
Linkens, D.A. "Computer Control for Patient Care", Computer Control of Real-Time Processes, IEE Control Engineering Series 41, 1990, Ch. 13, pp. 216-238.
Mako Hill et al., "The Official Ubuntu Book", Shoeisha Co., Ltd., 1st Edition, Jun. 11, 2007, pp. 115 to 125.
Marshall, et al., "New Microprocessor-Based Insulin Controller", IEEE Transactions on Biomedical Engineering, Nov. 1983, vol. BME-30, No. 11, pp. 689-695.
Martino et al., "Automation of a Medical Intensive Care Environment with a Flexible Configuration of Computer Systems", Proceedings of the Annual Symposium on Computer Application in Medical Care, Nov. 5, 1980, vol. 3, pp. 1562-1568.
Matsunaga et al., "On the Use of Machine Learning to Predict the Time and Resources Consumed by Applications", 2010 10th IEEE/ACM International Conference on Cluster, Cloud and Grid Computing (CCGrid), May 17-20, 2010, pp. 495-504.

Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.
"McKesson Automation and ALARIS Medical Systems Developing Point-of-Care Bar Coding Solution to Improve IV Medication Safety", PR Newswire, NY, Dec. 9, 2002, pp. 4.
Medfusion™, "Medfusion Syringe Infusion Pump Model 4000", Operator's Manual, Software Version V1.1, Sep. 2011, pp. 154. <http://www.medfusionpump.com/assets/literature/manuals/Operators_Manual_4000_40-5760-51A.pdf>.
Metnitz et al., "Computer Assisted Data Analysis in Intensive Care: the ICDEV Project-Development of a Scientific Database System for Intensive Care", International Journal of Clinical Monitoring and Computing, Aug. 1995, vol. 12, No. 3, pp. 147-159.
Micrel Medical Devices, "MP Daily +" <http://web.archive.org/web/20130803235715/http://www.micrelmed.com/index.aspx?productid=9> as archived Aug. 3, 2013 in 1 page.
Moghissi, Etie, MD, FACP, FACE, "Hyperglycemia in Hospitalized Patients", A Supplement to ACP Hospitalist, Jun. 15, 2008, pp. 32.
Murray, Jr. et al., "Automated Drug Identification System (during surgery)", IEEE Proceedings of Southeastcon '91, Apr. 7-10, 1991, pp. 265.
Nicholson et al., "'Smart' Infusion Apparatus for Computation and Automated Delivery of Loading, Tapering, and Maintenance Infusion Regimens of Lidocaine, Procainamide, and Theophylline", Proceedings of The Seventh Annual Symposium on Computer Applications in Medical Care, Oct. 1983, pp. 212-213.
Nolan et al., "The P1073 Medical Information Bus Standard: Overview and Benefits for Clinical Users", 1990, pp. 216-219.
Omnilink Systems, Inc., "Portable Medical Equipment Tracking", <http://www.omnilink.com/portablemedicalequipmenttracking/>, Mar. 15, 2015, pp. 2.
O'Shea, Kristen L., "Infusion Management: Working Smarter, Not Harder", Hospital Pharmacy, Apr. 2013, vol. 48, No. 3, pp. S1-S14.
Package Management in Debian GNU/Linux, Debian GNU/Linux Expert Desktop Use Special, Giutsu-Hyohron Co., Ltd., First Edition, Sep. 25, 2004, pp. 183-185.
Passos et al., "Distributed Software Platform for Automation and Control of General Anaesthesia", Eighth International Symposium on Parallel and Distributed Computing, ISPDC '09, Jun. 30-Jul. 4, 2009, pp. 8.
Philips, "IntelliSpace Event Management and IntelliVue Patient Monitoring", Release 10, 2011, <http://incenter.medical.philips.com/doclib/enc/fetch/2000/4504/577242/577243/577247/582646/583147/8359175/Philips_Patient_Monitoring_and_IntelliSpace_Event_Management_Interoperability.pdf%3fnodeid%3d8508574%26vernum%3d-2>, pp. 2.
Pretty et al., "Hypoglycemia Detection in Critical Care Using Continuous Glucose Monitors: An in Silico Proof of Concept Analysis", Journal of Diabetes Science and Technology, Jan. 2010, vol. 4, No. 1, pp. 15-24.
Rappoport, Arthur E., "A Hospital Patient and Laboratory machine-Readable Identification System (MRIS) Revisited", Journal of Medical Systems, Apr. 1984, vol. 8, Nos. 1/2, pp. 133-156.
Ritchie et al., "A Microcomputer Based Controller for Neuromuscular Block During Surgery", Annals of Biomedical Engineering, Jan. 1985, vol. 13, No. 1, pp. 3-15.
Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.
Sanders et al., "The Computer in a Programmable Implantable Medication System (PIMS)", Proceedings of the Annual Symposium on Computer Application in Medical Care, Nov. 2, 1982, pp. 682-685.
Schilling et al., "Optimizing Outcomes! Error Prevention and Evidence-Based Practice with IV Medications", A Pro-Ce Publication, Hospira, Inc., Feb. 6, 2012, pp. 56.
Schulze et al., "Advanced Sensors Technology Survey", Final Report, Feb. 10, 1992, pp. 161.
Scott, et al., "Using Bar-Code Technology to Capture Clinical Intervention Data in a Hospital with a Stand-Alone Pharmacy

(56) References Cited

OTHER PUBLICATIONS

Computer System", Mar. 15, 1996, American Journal of Health-System Pharmacy, vol. 53, No. 6, pp. 651-654.
Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.
Shabot, M. Michael, "Standardized Acquisition of Bedside Data: The IEEE P1073 Medical Information Bus", International Journal of Clinical Monitoring and Computing, vol. 6, Sep. 27, 1989, pp. 197-204.
Sheppard, Louis, Ph.D., "Automation of the Infusion of Drugs Using Feedback Control", Journal of Cardiothoracic and Vascular Anesthesia, Feb. 28, 1989, vol. 3, No. 1, pp. 1-3.
Sheppard, Louis, Ph.D., "Computer Control of the Infusion of Vasoactive Drugs", Annals of Biomedical Engineering, Jul. 1980, vol. 8, No. 4-6, pp. 431-444.
Sheppard, Louis, Ph.D., "The Application of Computers to the Measurement, Analysis, and Treatment of Patients Following Cardiac Surgical Procedures", The University of Alabama in Birmingham, Oct. 31, 1977, pp. 297-300.
Sheppard, Louis, Ph.D., "The Computer in the Care of Critically Ill Patients", Proceedings of the IEEE, Sep. 1979, vol. 67, No. 9, pp. 1300-1306.
"Sigma Spectrum: Operator's Manual", Oct. 2009, pp. 72. <http://static.medonecapital.com/manuals/userManuals/Sigma-Spectrum-Operator-Manual-Octover-2009.pdf>.
Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.
Siv-Lee et al., "Implementation of Wireless 'Intelligent' Pump IV Infusion Technology in a Not-for-Profit Academic Hospital Setting", Hospital Pharmacy, Sep. 2007, vol. 42, No. 9, pp. 832-840. <http://www.thomasland.com/hpj4209-832.pdf>.
Slack, W.V., "Information Technologies for Transforming Health Care", <https://www.andrew.cmu.edu/course/90-853/medis.dir/otadocs.dir/03ch2.pdf>, Ch. 2, 1995, pp. 29-78.
Smith, Joe, "Infusion Pump Informatics", CatalyzeCare: Transforming Healthcare, as printed May 12, 2011, pp. 2.
Sodders, Lisa, "VA Center Keeps Medicine in Right Hands", The Capital-Journal, Dec. 4, 1999, pp. 1-2.
"Software Versioning", Wikipedia.org, dated Oct. 16, 2011 in 11 pages, <https://en.wikipedia.org/w/index.php?title=Software_versioning&oldid=455859110>.
Stitt, F.W., "The Problem-Oriented Medical Synopsis: a Patient-Centered Clinical Information System", Proceedings of the Annual Symposium on Computer Application in Medical Care, 1994, pp. 88-92.
Stokowski, Laura A. RN, MS, "Using Technology to Improve Medication Safety in the Newborn Intensive Care Unit", Advances in Neonatal Care, Dec. 2001, vol. 1, No. 2, pp. 70-83.
Sutton et al., "The Syntax and Semantics of the PROforma Guideline Modeling Language", Journal of the American Medical Informatics Association, Sep./Oct. 2003, vol. 10, No. 5, pp. 433-443.
Szeinbach et al., "Automated Dispensing Technologies: Effect on Managed Care", Journal of Managed Care Pharmacy (JMCP), Sep./Oct. 1995, vol. 1, No. 2, pp. 121-127.
Szolovits et al., "Guardian Angel: Patient-Centered Health Information Systems", Technical Report MIT/LCS/TR-604, Massachusetts Institute of Technology Laboratory for Computer Science, May 1994, pp. 39.
Van Den Berghe, M.D., Ph.D., et al., "Intensive Insulin Therapy in Critically Ill Patients", The New England Journal of Medicine, Nov. 8, 2001, vol. 345, No. 19, pp. 1359-1367.
Van Den Berghe, M.D., Ph.D., et al., "Intensive Insulin Therapy in the Medical ICU", The New England Journal of Medicine, Feb. 2, 2006, vol. 354, No. 5, pp. 449-461.
Van Der Maas et al., "Requirements for Medical Modeling Languages", Journal of the American Medical Informatics Association, Mar./Apr. 2001, vol. 8, No. 2, pp. 146-162.
Villalobos et al., "Computerized System in Intensive Care medicine", Medical Informatics, vol. 11, No. 3, 1986, pp. 269-275.
Wilkins et al., "A Regular Language: The Annotated Case Report Form", PPD Inc., PharmaSUG2011—Paper CD18, 2011, pp. 1-9.
Ying et al., "Regulating Mean Arterial Pressure in Postsurgical Cardiac Patients. A Fuzzy Logic System to Control Administration of Sodium Nitroprusside", IEEE Engineering in Medicine and Biology Magazine, vol. 13, No. 5, Nov.-Dec. 1994, pp. 671-677.
Yue, Ying Kwan, "A Healthcare Failure Mode and Effect Analysis on the Safety of Secondary Infusions", Thesis, Institute of Biomaterials and Biomedical Engineering, University of Toronto, 2012, pp. 168.
Yurkonis et al., "Computer Simulation of Adaptive Drug Infusion", IEEE Transactions on Biomedical Engineering, vol. BME-34, No. 8, Aug. 1987, pp. 633-635.
Zakariah et al., "Combination of Biphasic Transmittance Waveform with Blood Procalcitonin Levels for Diagnosis of Sepsis in Acutely Ill Patients", Critical Care Medicine, 2008, vol. 36, No. 5, pp. 1507-1512.
International Search Report and Written Opinion received in PCT Application No. PCT/US2010/031351, dated Jun. 28, 2010 in 9 pages.
International Preliminary Report on Patentability and Written Opinion received in PCT Application No. PCT/US2010/031351, dated Oct. 27, 2011 in 8 pages.

\* cited by examiner

DEFINE ALARM INTEGRATION RULE SET — 500

NAME: POST-SURGICAL RESPIRATORY DEPRESSION DETECTION — 502

PARAMETERS AND CONDITIONS: — 504
- GROUP
  ("HIGH EtCO2" ALARM OCCURS) OR
  ("LOW RESP RATE" ALARM OCCURS) OR
  ("LOW SpO2" ALARM OCCURS AND PERSISTS FOR 5 MINUTES)
- OR
- (COMMUNICATION WITH PATIENT MONITOR IS LOST)

Buttons: ADD (506), DELETE (508), MODIFY (510), GROUP (512)

RESPONSES: — 514
- ☒ UPDATE CENTRAL MONITOR
- ☒ ISSUE REMOTE NOTIFICATION
- ○ DECREASE INFUSION RATE BY 25%
- ○ DECREASE INFUSION RATE BY 50%
- ○ DECREASE INFUSION RATE BY 75%
- ⦿ PAUSE INFUSION
- ☐ SWITCH ALGORITHM TO...

OK    CANCEL

FIG. 4

SYSTEM AND METHOD FOR CONFIGURING A RULE SET FOR MEDICAL EVENT MANAGEMENT AND RESPONSES

CROSS-REFERENCE TO RELATED APPLICATIONS

The present application is a continuation application of U.S. patent application Ser. No. 17/238,780, filed Apr. 23, 2021, now U.S. Pat. No. 11,654,237, which is a continuation application of U.S. patent application Ser. No. 16/266,622, filed Feb. 4, 2019, now U.S. Pat. No. 11,013,861, which is a continuation application of U.S. patent application Ser. No. 15/467,903, filed Mar. 23, 2017, now U.S. Pat. No. 10,238,801, which is a continuation application of U.S. patent application Ser. No. 13/586,615, filed Aug. 15, 2012, now U.S. Pat. No. 9,604,000, which is a divisional application of U.S. patent application Ser. No. 12/761,107, filed Apr. 15, 2010, now U.S. Pat. No. 8,271,106, which claims priority under 35 U.S.C. 119 of U.S. Ser. No. 61/170,205 filed on Apr. 17, 2009, the disclosures of each of which are hereby incorporated by reference in their entireties.

FEDERALLY SPONSORED RESEARCH OR DEVELOPMENT

None.

TECHNICAL FIELD

The present invention relates to medical monitoring systems for monitoring hospital patients and patient care equipment based on a variety of parameters and conditions associated with monitored biometric or physiological information and equipment information and for providing user-defined responses to those parameters and conditions.

BACKGROUND AND SUMMARY OF THE INVENTION

Modern medical care often involves the use of medication management systems, which include medication delivery and monitoring devices such as medication delivery pumps and/or patient parameter monitors. Medication management systems for configuring, controlling, and monitoring medication delivery devices have been disclosed. For example, commonly owned U.S. patent application Ser. No. 10/930,358, which published as US20050144043A1 on Jun. 30, 2005 and U.S. patent application Ser. No. 10/783,573, which published as US20050278194A1 on Dec. 15, 2005, disclose a medication management system wherein customizable drug library or medical device configuration information is prepared using a drug library editor (DLE) program and module of a medication management unit (MMU). The MMU downloads the customizable drug library to the medication delivery pump and receives status or activity information from the pump. Commonly owned U.S. patent application Ser. No. 10/783,877, which published as WO2005050526A2 on Jun. 2, 2005, discloses how the drug library or medical device configuration information is created, edited, stored and communicated to a medication delivery device in the context of a medication management system to deliver substances, such as fluids and/or fluid medication to patients.

According to the above-mentioned commonly owned published patent applications, a typical medication management system includes a point of care computer, such as a barcode point of care computer and/or pharmacy computer, and/or an MMU, in communication with one or more medication delivery devices. The point of care computer(s) and/or the MMU, with associated memory, store various information, such as patient information, prescription information, customized drug library or other information, for managing medication delivery to a patients, such as performing five-rights checking, configuring the medication delivery devices, and receiving and storing activity information received from the medication delivery devices.

Caregivers use outputs from patient monitoring and equipment monitoring devices to make various patient care decisions. Patient monitoring devices and patient care equipment monitoring devices may be connected to a receiver, which receives the output signals from the patient monitoring devices and patient care equipment monitoring devices. In some cases, the receivers may display and/or record the information from the patient and patient care equipment monitoring devices. In other cases, the devices may include a monitor and/or recording medium. The receivers or devices may also have preset or adjustable alarms that are triggered when one of the outputs from the patient or patient care equipment monitoring devices deviates from a pre-set limit.

One drawback of such conventional monitoring systems is the occurrence of false positive alarms. Such false positive alarms may occur due to a momentary deviation of a monitored state that deviates from the pre-set limits, but which rapidly returns to a normal state. For example, one application of such a conventional alarm monitoring system is for use in monitoring a patient's reaction to a controlled administration of analgesia. In such systems, currently practiced technologies are subject to the following problems: (1) false alarms due to erroneous respiratory or blood gas readings associated with motion artifacts or poor sensor placement and coupling; and (2) false alarms resulting from patient circumstances in which monitored conditions are not truly indicative of an adverse event. Such an alarm may be triggered, for example, if a patient monitor is briefly disconnected from a monitoring device. False positive alarms waste the time of hospital personnel who need to respond to such alarms. Frequent false positive alarms may also desensitize medical responders to the alarm. In addition, a false positive alarm may cause a medial responder to take improper action believing that the alarm is a true alarm.

Another drawback of such conventional systems is the relative lack of ability to require a response only when there has been a change in multiple monitored parameters, such as a change in blood oxygen levels coupled with a change in breathing. Specifically, for monitoring analgesic application via a pump, alarms are typically associated with univariate parameters, such as $SpO_2$ alone or end tidal $CO_2$ ($ETCO_2$) alone, for detecting changes in these parameters consistent with respiratory depression. These systems are subject to a variety of problems due to the complexity of the body's response to analgesia and the insufficiency of a single variable to represent the range of clinical circumstances and patient parameters that may result from the administration. For example, an undesirable adverse event associated with administration of analgesics, sedatives and anesthetics can be depression of the patient's respiratory and/or central nervous systems. Exacerbating the risk to patients is the profound variation in drug efficacy between patients and through time. Consequently, avoidance of drug overdose is of particular concern to healthcare professionals and can result in the under administration of narcotics. The latter problem leads to unnecessary and significant discomfort and is associated with longer hospital stays and recovery times.

Yet another drawback of such systems is the difficulty of creating a readily customized rule set for monitoring, alarming and requiring responses thereto. Additionally, these systems typically lacked the ability to automatically respond to changes in a plurality of monitored conditions. Furthermore, such traditional systems often lacked the ability to automatically change from a first rule set to a second rule set based on a change in the monitored parameters.

The system disclosed herein is designed to enable hospital personnel to configure a rule set by inputting, via a user-interface, a wide variety of monitored patient or equipment parameters, and conditions associated with those parameters, which, when satisfied by inputs from the medical equipment and patient monitoring devices, trigger a user-defined or user-selected response. The rule set can include Boolean combinations of these parameters and respective conditions to establish a set of multi-variable inputs that must occur before a response is triggered. Authorized hospital personnel can also customize the type of parameter, the conditions for that parameter to be met and type of response for each rule set. The software utilized to implement this invention may use a context free grammar, specifically, Backus-Naur form metasyntax, to build the rule sets comprised of parameters, conditions and responses.

All of the patents and patent application referred to within this Background of the Invention section of the present specification are hereby incorporated by reference and made a part of this specification. In addition, the present invention is provided to solve the problems discussed above and, to provide advantages and aspects not provided by medical systems, as well as achieve other objects not explicitly stated above. A full discussion of the features, advantages and objects of the present invention is deferred to the following detailed description, which proceeds with reference to the accompanying drawings.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings in which:

FIG. 4 is one embodiment of an exemplary interface screen display for configuring a rule set for use with a medication delivery device and patient monitoring system of the present invention.

DETAILED DESCRIPTION OF THE INVENTION

Figure 1:
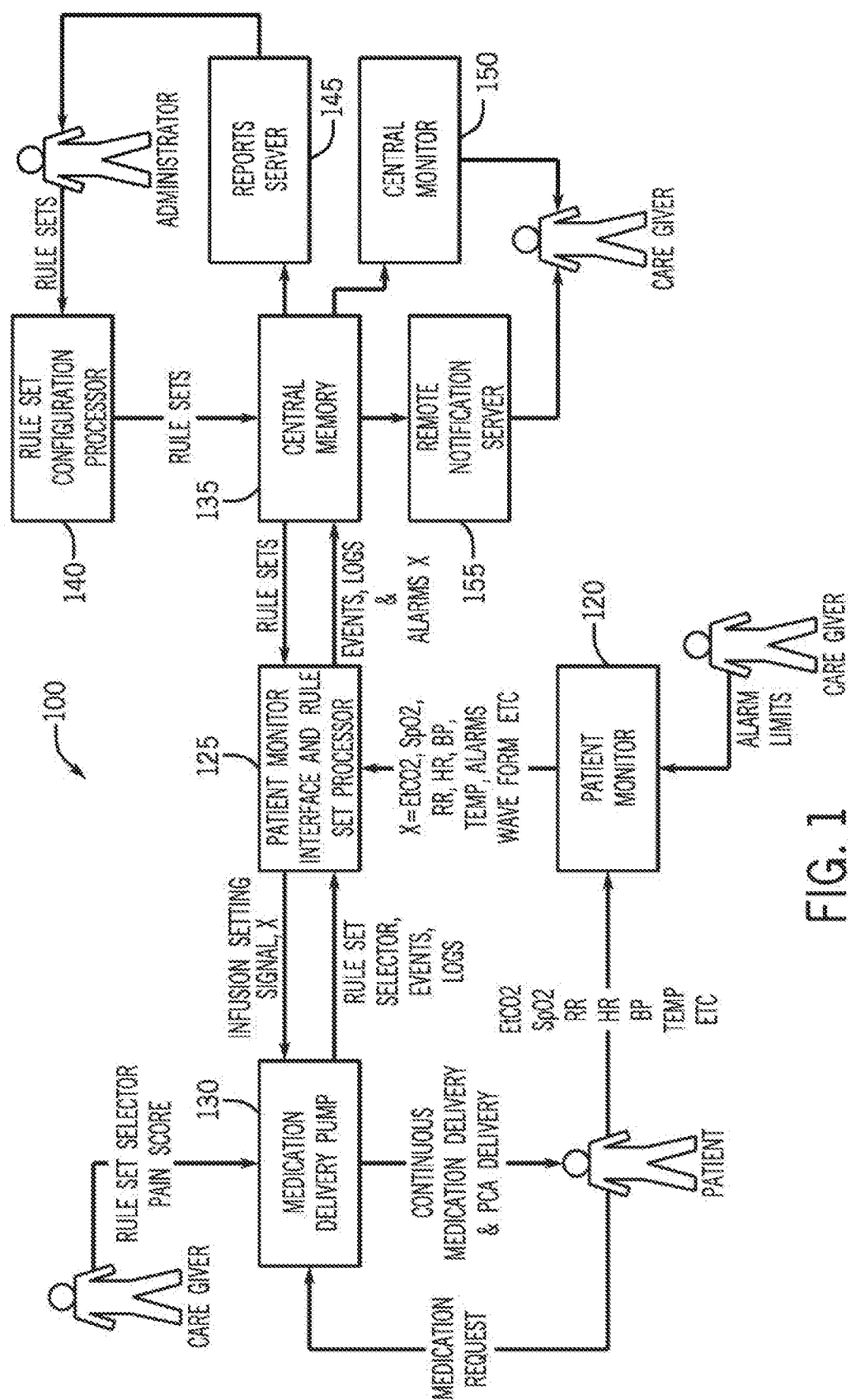
FIG. 1 is a diagram of one embodiment of a medication delivery device and patient monitoring system of the present invention.

While this invention is susceptible of embodiments in many different forms, there is shown in the drawings and will herein be described in detail preferred embodiments of the invention with the understanding that the present disclosure is to be considered as an exemplification of the principles of the invention and is not intended to limit the broad aspect of the invention to the embodiments illustrated.

FIG. 1 shows an exemplary medical monitoring system for monitoring hospital patients and patient care equipment. As shown in FIG. 1, a medication management system 100 includes a patient monitor 120 for monitoring patient biometric or physiological information of various types. For example, the monitored information can include, but is not limited to, $ETCO_2$, $SpO_2$, respiratory rate, heart rate, blood pressure, temperature and other patient biometric, physiological or medical parameter information. The patient monitor may include appropriate biometric sensors for sensing the desired patient information, as known in the art. Such biometric sensors may include an EKG system, respiratory monitors, blood gas monitors, glucose monitors, blood analyte monitors and/or other measurement systems which monitor a physiological variables or analytes associated with a patient. For example, in the case of a system for patient controlled analgesia (PCA), a NELLCOR or MASSIMO monitor with an ORIDION capnography respiratory monitor board can be used to generate data, waveforms, and alarms associated with heart rates, $SpO_2$ levels, respiratory rates and $ETCO_2$ levels.

The patient monitor 120 can optionally include a processor and patient monitoring application for monitoring the information received by the various biometric sensors. Patient monitor 120 may include a user interface associated therewith to receive input from a patient or caregiver. A patient monitor processor compares the information received from the sensors and generates an alarm signal based on the comparison. Alarm signals can be generated if an alarm limit is met, or alternately when the alarm limit is exceeded. Alarm limits can include an upper limit, a lower limit, or both upper and lower limits that together define one or more acceptable ranges. Patient monitor 120 is communicatively networked with a patient monitor interface and rule set processor 125 for transmitting the monitored information and/or alarms to the patient monitor interface and rule set processor 125.

As shown in FIG. 1, a patient care device, which is shown as a medication delivery pump 130, may be operatively connected to or in communication with the patient. The medication delivery pump 130 may be configured for controlled delivery of a medication to the patient. The medical pump can be used with PCA (patient controlled analgesia) request devices in which a patient can "self-deliver" medication, such as an analgesia or analgesic. For example, U.S. Pat. No. 4,551,133, to Zeggers de Beyl et al., issued Nov. 5, 1985, and incorporated in its entirety herein by reference, discloses a patient controlled analgesia system for introducing medication to a peripheral vein of a patient. The delivery of the analgesic is controlled by a microprocessor based system in response to the patient's requests. Specifically, the microprocessor is associated with a remote patient control or PCA request device, for providing an actuation signal to the microprocessor when the patient requests a delivery of medication.

The system 100 may further have a plurality of medication delivery pumps 130 for the administration of a plurality of medications. The medication delivery pump may further include a user interface that permits a caregiver to provide inputs to the medication delivery pump 130. Such inputs may include a pain score associated with the patient, which may be used to determine the amount and frequency of patient controlled analgesic (PCA) permitted. In one embodiment, the medication delivery pump has a user interface configured to permit a caregiver to select a rule set, herein sometimes referred to as an algorithm, for monitoring the patient and patient care equipment and responding to inputs from the patient and patient care equipment, as described in greater detail below. In addition, the user interface on the medication delivery pump 130 provides a means, such as a push button or a touch screen interface, for a caregiver to respond to an alarm or an infusion event (for example, an infusion pause).

The medication delivery pump 130 is in communication with the patient monitor interface and rule set processor 125 for communicating information between the medication delivery pump 130, the patient monitor interface and rule set processor 125, the patient monitor 120, and other components of the system 100 as described below. As a result, medical pump information can be communicated from the medication delivery pump 130 to other components of the system 100. Such medical pump information may include both medical pump status information and medical event information. Medical pump status information can include but is not limited to whether an active delivery of medication is taking place, the rate of the delivery, volume (delivered or remaining to be delivered) and the length of time passed since the delivery began. Medical pump event information can include but is not limited to whether any alarms or alerts have issued since the last communication, whether an occlusion has taken place, and whether power was lost to the medical pump, among other medical pump event information. Status information and/or medication delivery status information is used herein to refer to at least medical pump status information, medical pump event information, and/or other status and/or event information. The medical delivery status information may be transmitted as historical logs of information or real time communication or information.

The medication delivery pump 130 may also communicate the rule set selected by a caregiver at the medication delivery pump 130 to the patient monitor interface and rule set processor 125. The patient monitor interface and rule set processor 125 is communicatively connected with a central memory 135, which has a library of rule sets or portions thereof stored therein. The library of rule sets can be a part of a customizable drug library or other libraries that can be downloaded to medical devices. In one embodiment, the patient interface and rule set processor 125 applies the selected rule set to the information received from the patient monitor 120, such as $ETCO_2$, $SpO_2$, respiratory rate, heart rate, blood pressure, temperature and other patient parameter information, and/or the information received from the medication delivery pump 130, such as the medical delivery status information, to the rule set. Depending upon whether the conditions and parameters of the rule set are satisfied, the patient interface and rule set processor 125 may generate an output signal to the medication delivery pump 130 that instructs the medication delivery pump to adjust the medication delivery in some manner.

In another embodiment, the patient monitor interface and rule set processor 125 may send information from the patient monitor 120 to the medication delivery pump 130 without processing it through a rule set. The medication delivery pump 130 or the patient monitor 120 may be configured to receive alarm limits inputted by a caregiver. The alarm limits may correspond to the patient information received at the medication delivery pump 130. Alternatively, or additionally, the alarm limits may relate to information regarding the medication delivery pump 130 itself. A pump processor compares the selected alarm limits to the relevant information, and, if the information satisfies (meets, exceeds, falls under or between) the alarm limits, generates an alarm signal from the pump 130. The alarm signal from the pump may be conveyed to the patient monitor and rule set processor 125 and to other components of the system 100 as described below.

The medication delivery pump 130 may display the patient information on a display screen of the medication delivery pump. The display screen may also display a variety of medical pump status information including but not limited to a patient identifier, room number, delivery mode, delivery rate, whether an active delivery of medication is taking place, how long since the delivery began, basal rate, PCA bolus amount, lockout period for the PCA bolus, and lockout volume for the PCA bolus.

In an alternative embodiment that will be easily understood by one skilled in the art in view of the figures and description herein, the patient monitor interface and rule set processor 125 could be a part of either the medication delivery pump 130 or the patient monitor 120 or another component of the system rather than a separate unit. Processing capacity and functions can be distributed among the components of the system 100 as shown and described or they can be rearranged and/or combined within any of the other processors in the system.

The central memory 135 is in communication with a rule set configuration processor 140. The rule set configuration processor 140, which may be a personal computer, personal digital assistant (PDA) or the like, has a user input that permits an administrator to create and configure a rule set, sometimes referred to herein as an algorithm, as described in greater detail below. The rule set is then sent to and stored in the central memory 135.

The central memory 135 also may receive certain information from the patient monitor interface and rule set processor 125. Specifically, the central memory 135 may receive logs of the patient information generated by the patient monitor 120 and the medication delivery pump information generated by the medication delivery pump 130. This information may also be sent to the central memory 135 from the patient monitor interface and rule set processor 125 in real time.

The central memory 135 may also store information related to the patient's medical history and recent medical treatments, and, in particular, the patient's recent history of infused medication. This information may be accessed by the patient monitor interface and rule set processor 125 or any other component of the system 100 when such information is required as an input for processing a rule set. For example, a rule set may require inputs regarding the amount of a drug still active in the patient, which could be determined based on the amount of the drug that the patient has received and how recently the drug was delivered to the patient, which would be stored in the central memory 135. A detailed example of such a rule set is described below.

The central memory 135 may also receive outputs from the patient monitor interface and rule set processor 125 that are generated as a response to processing inputs via a rule set. Specifically, if the parameters and associated conditions of a certain rule set are satisfied, the patient monitor interface and rule set processor 125 may send an alarm instruction to the central memory 135, which may then be sent to a caregiver, as described below. In another example, if the parameters and conditions of a rule set are satisfied, the patient monitor interface and rule set processor 125 may send a signal to the central memory 135 to access a different rule set stored in the central memory 135.

The central memory 135 may further distribute the information that it receives from the patient monitor interface and rule set processor 125 to a reports server 145, a central monitor 150 and a remote notification server 155. In particular, the reports server 145 may receive summaries, overviews and logs of the medication delivery pump information and the patient monitor information for generating reports that can be sent to or made available to administrators. The central monitor 150 may receive similar information for displaying information from the medication delivery pump 130 and patient monitor 120 and provide this information to a caregiver at a location remote from the patient. The remote notification server 155 will typically receive instructions to notify caregivers of certain changes in patient or equipment status. For example, if the parameters and conditions of a rule set are satisfied and the rule set dictates that a caregiver should be notified in such an event, the remote notification server 155 will generate a notification to the caregiver. Such notifications may be conveyed to one or more small personal digital assistant computers including but not limited to a pager, cell phone or PDA that is in communication with the remote notification server 155. The small digital assistant computers can be carried by the caregivers and used by them to identify themselves through the use of built in barcode scanners or otherwise as they perform certain caregiving functions, such as performing scheduled rounds in which the caregivers deliver medication to patients in patient rooms within a caregiving facility.

In an alternative embodiment, the reports server 145, central monitor 150 and remote notification server 155, or any combination of these devices may be networked directly to the patient monitor interface and rule set processor 125, the pump 130 and/or the patient monitor 120.

Communication of information between the various components of the system may occur in a variety of ways. Information may be communicated between the various devices in a real-time constant stream, the information may be pushed from the sending to device to the receiving device on a periodic basis or on a continuous loop, the information may be pulled from the sending device by the receiving device on a periodic basis or on a continuous loop, and/or the various devices may be configured to push or pull the information based on various triggering events, for example, the passage of time or once a certain amount of information has been accumulated. The components of the system shown in FIG. 1 are described in greater detail below.

The medication delivery pump or medical pump 130 includes but is not limited to enteral pumps, infusion pumps, cassette pumps, syringe pumps, peristaltic pumps, or any fluid pumping device for the delivery of fluids intravenously, intra-arterially or otherwise to a patient. A pump processing unit or pump processor may be included in pump 130 and performs various operations, as described in greater detail herein. An input/output device or user interface communicates with the pump processing unit and allows the user to receive output from pump processing unit and/or input information or commands into the pump processing unit. Those of ordinary skill in the art will appreciate that input/output device may be provided as a separate display device and/or a separate input device. For example, in one embodiment of the present invention, the medical pump 130 includes a patient-controlled analgesia (PCA) request device which is in electrical communication with the processor, for receiving an input from a person to generate a medication request signal from the PCA request device.

A pump memory communicates with the pump processor and stores code and data necessary for the pump processor to calculate and output the operating parameters of the pump 130. The pump memory stores a programming code, such as a medication delivery programming code or application for processing data to determine and control the operating parameters of the medical pump 130.

With continued reference to FIG. 1, the medical pump 130 can also include a communications engine or interface, in electrical communication with the pump processor, for transmitting/receiving communications between the pump processor, the patient parameter monitor 120, and the patient monitor interface and rule set processor 125, as described in detail herein. In fact, in one embodiment where the rule set processing function is integrated into the pump 130, the communication engine also serves as the patient monitor interface.

The central memory 135 can include a central programming code, such as a central medication management application and/or central patient monitoring application and other applications, for execution by the central processor, which can perform various medication management, patient monitoring, and other functions, as described in greater detail herein. Further, the medical pump 130 can include many aspects of a LifeCare PCA® Infusion System, and the medication management application within the central memory 135 can include many aspects of Hospira MedNet® Software, both manufactured and sold by Hospira, Inc., the assignee of the present invention, in conjunction with the present invention.

Generally, in terms of hardware architecture, as shown in FIG. 1, the medical pumps 130, patient parameter monitors 120, patient monitor interface and rule set processor 125, rule set configuration processor 140, central monitor 135, reports server 145, and remote notification server 155 of the medication management and/or patient parameter monitoring systems 100, may each include a processor, memory, and one or more input and/or output (I/O) devices (or peripherals) that are communicatively coupled via a local interface. The local interface can be, for example, but not limited to, one or more buses or other wired or wireless connections, as is known in the art. The local interface may have additional elements, such as cables, controllers, buffers (caches), drivers, repeaters, and receivers, to enable communications. Further, the local interface may include address, control, and/or data connections to enable appropriate communications among the other computer components.

The processors are hardware devices for executing software, particularly software stored in memory. The processors can be any custom made or commercially available processor, a central processing unit (CPU), an auxiliary processor among several processors associated with the medical pumps 130, patient parameter monitors 120, patient monitor interface and rule set processor 125, rule set configuration processor 140, central monitor 150, reports server 145 and remote notification server 155 of the medication management and/or patient parameter monitoring system 100, a semiconductor based microprocessor (in the form of a microchip or chip set), a macroprocessor, or generally any device for executing software instructions. Examples of suitable commercially available microprocessors are as follows: a PA-RISC series microprocessor from Hewlett-Packard Company, an 80x86 or Pentium series microprocessor from Intel Corporation, a PowerPC microprocessor from IBM, a Sparc microprocessor from Sun Microsystems, Inc., or a 68xxx series microprocessor from Motorola Corporation. The processors may also represent a distributed processing architecture such as, but not limited to, EJB, CORBA, and DCOM. In one embodiment, the central memory 135 and reports server 145 is on a WINDOWS based server or series of servers.

Each memory of each of the medical pumps 130, patient parameter monitors 120, patient monitor interface and rule set processor 125, rule set configuration processor 140, central monitor 150, reports server 145 and remote notification server 155 of the medication management and/or patient parameter monitoring systems 100, can include any one or a combination of volatile memory elements (e.g., random access memory (RAM, such as DRAM, SRAM, SDRAM, etc.)) and nonvolatile memory elements (e.g., ROM, hard drive, tape, CDROM, etc.). Moreover, these memories may incorporate electronic, magnetic, optical, and/or other types of storage media. The memories can have a distributed architecture where various components are situated remote from one another, but are still accessed by the processors of the medical pumps 130, patient parameter monitors 120, patient monitor interface and rule set processor 125, rule set configuration processor 140, central monitor 150, reports server 145, and remote notification server 155 of the medication management and/or patient parameter monitoring system 100.

The software within one or more of the above referenced memories may include one or more separate programs. The separate programs comprise ordered listings of executable instructions for implementing logical functions. In the examples of FIG. 1, the software in the memories can include suitable operating systems (O/S). A non-exhaustive list of examples of suitable commercially available operating systems for at least some of these devices is as follows: (a) a WINDOWS operating system available from Microsoft Corporation; (b) a NETWARE operating system available from Novell, Inc.; (c) a MACINTOSH operating system available from Apple Computer, Inc.; (d) a UNIX operating system, which is available for purchase from many vendors, such as the Hewlett-Packard Company, Sun Microsystems, Inc., and AT&T Corporation; (e) a LINUX operating system, which is freeware that is readily available on the Internet; or (f) a run time VXWORKS operating system from WindRiver Systems, Inc. The operating systems essentially control the execution of other computer programs, such as the medication delivery applications, network interface applications, patient monitoring applications, central medication management applications, central patient monitoring applications, and/or biometric applications, in accordance with the present invention, and provide scheduling, input-output control, file and data management, memory management, and communication control and related services.

The I/O devices referred to above may include input devices, for example input modules for PLCs, a keyboard, mouse, scanner, microphone, touch screens, interfaces for various medical devices, bar code readers, biometric receivers, PCA request devices, stylus, laser readers, radio-frequency device readers, etc. Furthermore, the I/O devices may also include output devices, for example but not limited to, output modules for PLCs, a printer, bar code printers, displays, etc. Finally, the I/O devices may further include devices that communicate both inputs and outputs, for instance but not limited to, a modulator/demodulator (modem; for accessing another device, system, or network), a radio frequency (RF) or other transceiver, a telephonic interface, a bridge, and a router.

Figure 2:
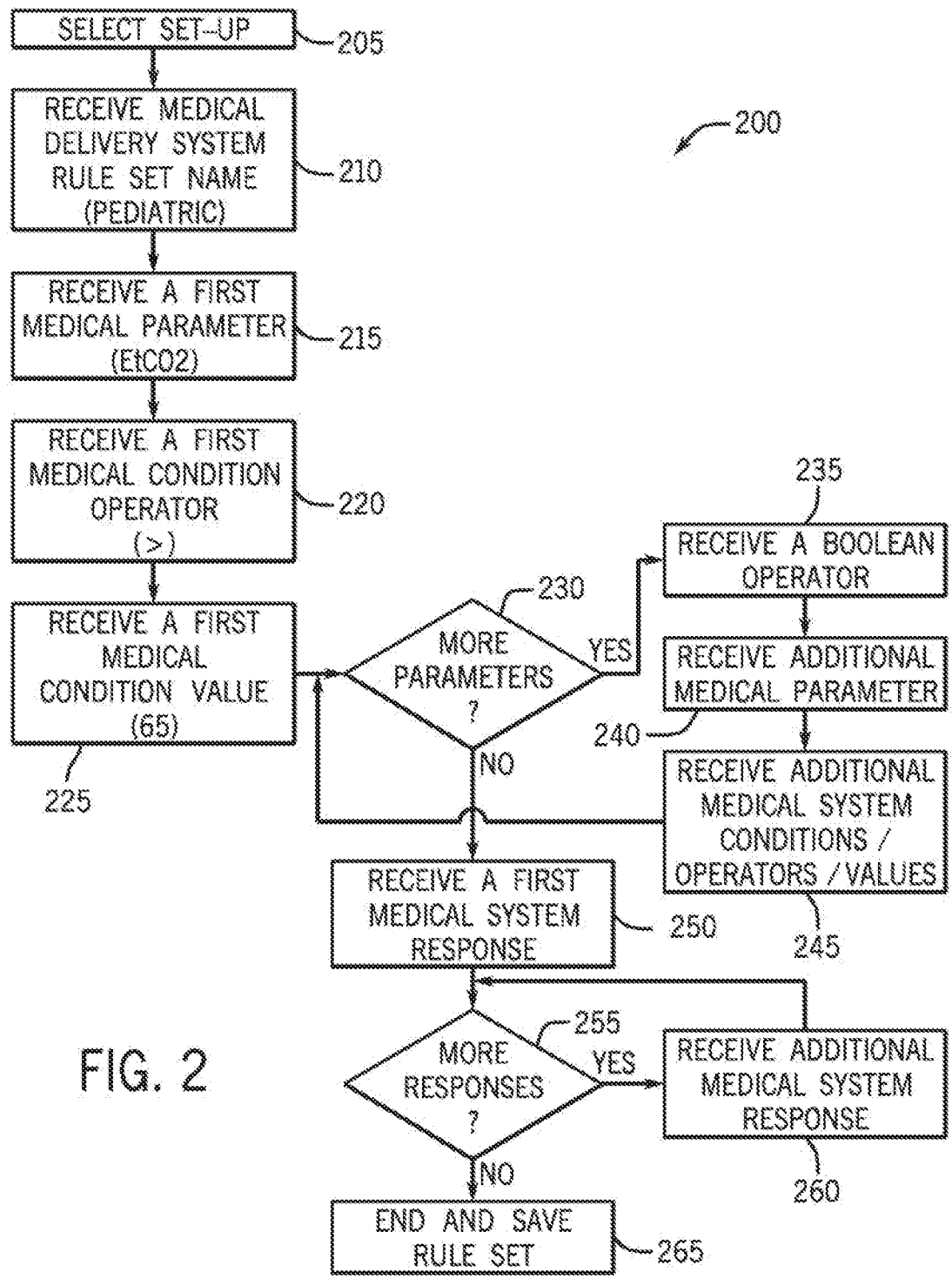
FIG. 2 is a flow chart of one embodiment of a system and method for configuring a rule set for use with a medication delivery device and patient monitoring system of the present invention.
Figure 3:
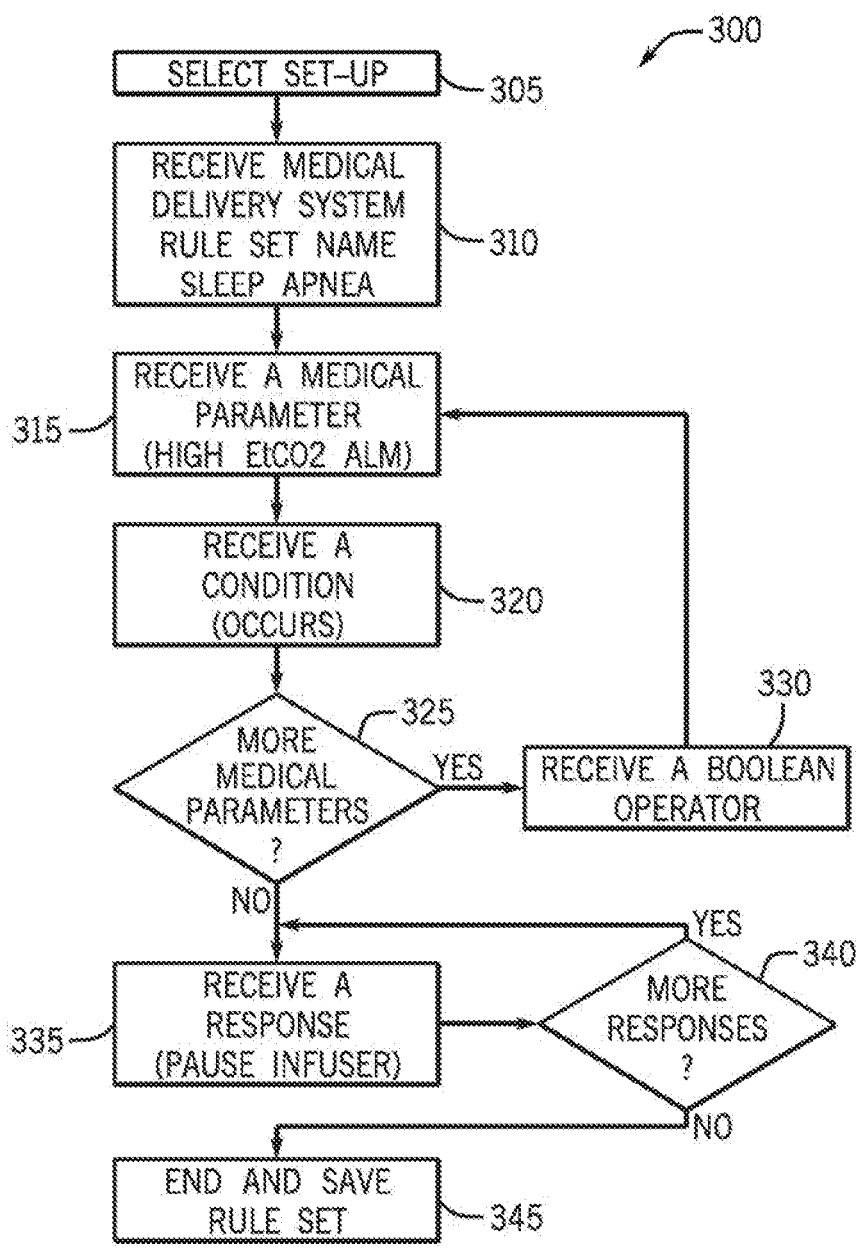
FIG. 3 is a flow chart of a second embodiment of a system and method for configuring a rule set for use with a medication delivery device and patient monitoring system of the present invention.

If the medical pumps 130, patient parameter monitors 120, patient monitor interface and rule set processor 125, rule set configuration processor 140, central monitor 150, reports server 145, and remote notification server 155 of the medication management and/or patient parameter monitoring system 100 are a PC, workstation, PDA, or the like, the software in the respective memories may further include a basic input output system (BIOS) (not shown in FIGS. 1, 2 and 3). The BIOS is a set of essential software routines that initialize and test hardware at startup, start the O/S, and support the transfer of data among the hardware devices. The BIOS is stored in ROM so that the BIOS can be executed when the medical pumps 130, patient parameter monitors 120, patient monitor interface and rule set processor 125, rule set configuration processor 140, central monitor 150, reports server 145, and remote notification server 155 of the medication management and/or patient parameter monitoring system 100 are activated.

When the medical pumps 120, patient parameter monitors 130, patient monitor interface and rule set processor 125, rule set configuration processor 140, central monitor 150, reports server 145, and remote notification server 155 of the medication management and/or patient parameter monitoring system 100, are in operation, the processors therein are configured to execute software stored within respective memories, to communicate data to and from memories, and to generally control operations of the components of the medication management and/or patient parameter monitoring system 100, pursuant to the software. The medication delivery applications, network interface applications, patient monitoring applications, central medication management applications, central patient monitoring applications, and/or biometric applications, and the O/S, in whole or in part, but typically the latter, are read by respective processors, perhaps buffered within the processors, and then executed.

When the medication management and/or patient parameter monitoring system 100 is implemented in software, as is shown in FIGS. 1, it should be noted that the application programs therein can be stored on any computer readable medium for use by or in connection with any computer related system or method. In the context of this document, a computer readable medium is an electronic, magnetic, optical, or other physical device or means that can contain or store a computer program for use by or in connection with a computer related system or method. In the context of this document, a "computer-readable medium" can be any means that can store, communicate, propagate, or transport the program for use by or in connection with the instruction execution system, apparatus, or device. The computer readable medium can be for example, but not limited to, an electronic, magnetic, optical, electromagnetic, infrared, or semiconductor system, apparatus, device, or propagation medium. More specific examples (a non-exhaustive list) of the computer-readable medium would include the following: an electrical connection (electronic) having one or more wires, a portable computer diskette (magnetic), a random access memory (RAM) (electronic), a read-only memory (ROM) (electronic), an erasable programmable read-only memory (EPROM, EEPROM, or Flash memory) (electronic), an optical fiber (optical), and a portable compact disc read-only memory (CDROM) (optical). Note that the computer-readable medium could even be paper or another suitable medium upon which the program is printed, as the program can be electronically captured, via, for instance, optical scanning of the paper or other medium, then compiled, interpreted or otherwise processed in a suitable manner if necessary, and then stored in a computer memory.

As referenced above, an administrator, also referred to herein as an authorized user, may configure a rule set for use with the system 100 at a rule set configuration processor 140. A rule set includes one or more parameters, for example patient physiological or biometric parameters, which may have conditions associated with the respective parameters, and one or more responses.

Methods of creating, establishing, or receiving a rule set configuration 200 and 300 are shown in FIGS. 2 and 3, respectively and understood in view of FIG. 1. The rule set configuration processor 140 receives an instruction from the administrator to set up a new rule set at steps 205, 305. The rule set configuration processor 140 then receives a rule set name entered or selected by the user, for example "Pediatric" or "Sleep Apnea" at steps 210, 310. The rule set configuration processor 140 then receives a first medical system parameter entered by the user at steps 215, 315. The parameters may be associated with one of the types of information received by the patient monitor from the biometric sensors, such as the $ETCO_2$, $SpO_2$, respiratory rate or heart rate. The parameters may also relate to an alarm received from the patient monitor 120, for example, a "low blood pressure" alarm. The parameters could also relate to information received from the medication delivery pump 130 or an alarm from the medication delivery pump. After receipt of the medical parameter, a condition associated with that medical parameter and inputted by the authorized user is received. As shown at steps 220 and 225, where the parameter relates to a numerical value rather than a binary event, the condition may be comprised of a first medical condition operator, for example ">", "<", "=", or "≠" followed by a first medical condition value. As shown in FIG. 3 in step 320, when the medical parameter relates to a binary event, such as an alarm, after receipt of the medical parameter, the condition may be a simple binary state related to the parameter, such as "occurs" ("occurred") or "does not occur" ("has not occurred"). However, such conditions may, in some cases, have additional limitations, such as "occurs and persists for 30 seconds." Various possibilities come to mind in view of these examples in the context of the present specification.

As shown at steps 230, 325, the rule set configuration processor 140 is configured to optionally receive additional parameters, condition operators and/or condition values. If the administrator opts to enter additional parameters, conditions, and/or condition values, the administrator enters, and the rule set configuration processor 140 receives, a Boolean operator, for example including but not limited to AND, OR, NOT, etc. for connecting the multiple parameters, conditions, and/or condition values shown at steps 235, 330 and optionally additional parameters, conditions, and/or condition values as shown at steps 240, 245, 315, 320. As can be understood in view of FIGS. 3 and 4, one example of the second parameter/condition/value could be that a $SpO_2$ alarm occurs and persists for five minutes. One skilled in the art will recognize that this latter complex type of parameter/condition/value state can itself be expressed or comprised of two separate, simpler states connected by a Boolean operator. For example, the first state can be expressed simply as a $SpO_2$ alarm occurs and the second state can be expressed as a $SpO_2$ alarm has persisted for more than five minutes. The two states can be connected by the Boolean operator AND. Alternatively, such complex states can be expressed through use of an optional decision block and loop through the conditions and/or values within the parameter of interest. States can be expressed in a variety of ways including but not limited to that a condition occurs X times in Y seconds or for X of the last Y seconds. Other units of time such as minutes or hours could be selected by the user to configure the rule set.

Once all of the parameters have been received, the rule set configuration processor 140 is configured to receive a first medical system response, as shown at steps 250, 335, entered by the administrator. The medical system responses may include the generation of an update to a central monitoring system, generation of a prompt to a caregiver requiring input from the caregiver, or an automated adjustment of a patient care device. For example, one such response might be to send a message to the caregiver suggesting an alternate form of treatments. Another such response is to send a signal to the medication delivery pump instructing it to pause an infusion or modify the rate of infusion, for example by decreasing it. Yet another response can include a call to the central memory to retrieve a different, previously entered, rule set and to implement that different rule set. The call can be based on the name of the different rule set that has previously been created and stored, and therefore has a name to use to refer to it within the call process. As shown in steps 255, 260, and 335, 340, a user may enter a plurality of responses. Once all conditions and responses have been received by the rule set configuration processor 140, the configuration process is complete and the rule set is then saved at steps 265, 345.

Flexibility in permitting authorized users to configure rule sets that incorporate a variety of parameters, conditions and responses can be achieved by using a context free grammar such as a Backus Naur Format (BNF) code. A partial listing of an exemplary BNF code for building the rule sets is listed in Appendix A, hereto.

In the exemplary grammar in Appendix A, variables, which are referred to herein as non-terminal symbols are shown in angled brackets <and >. (It should be noted that use of the <conditions> symbol in the exemplary grammar in Appendix A is not intended to have the same meaning as the term "conditions" as used within other portions of the specification.) Each non-terminal symbol can be comprised of a number of alternatives. The alternatives for the non-terminal symbol are listed after the ::=sign and each alternative is separated by the I symbol. The alternatives may themselves be non-terminal symbols or they may be terminal symbols that are shown in quotes. The alternatives may also comprise both a non-terminal portion and a terminal portion. For the convenient reference, the convention of indicating non-terminal symbols in angled brackets and terminal symbols in quotes is used in the description herein. The exemplary grammar for constructing a rule is further described below.

The grammar in the example shown provides for an alarm integration algorithm that includes at least one algorithm name, one or more conditions, and one or more do statements that include one or more responses. The algorithm name, the conditions symbol and the responses symbol are all non-terminal symbols (as indicated in the grammar above by the fact that these terms are provided in angled brackets <and >) that can be satisfied by a plurality of alternatives that are provided for each of these non-terminal symbols. For the <algorithm name> symbol, the alternatives comprise a bracketed string of characters, which is a string of characters surrounded by square brackets [ ]. The <condition> symbol may be satisfied by a single condition alternative or more than one condition alternative. For the <condition> symbol, the condition symbol alternatives comprise alarm and equipment parameters and associated conditions. These condition symbol alternatives may have one or more non-terminal symbols. For example, the condition symbol alternatives in the above-described grammar have the non-terminal symbols <alarm>, <count>, <duration> and <device>. Alternatively, some of the condition alternatives may be terminal. For example, one such terminal parameter satisfying the <condition> symbol may be "power is lost." The <alarm> symbol may be satisfied by either the entry of an <alarm-type>, which is non-terminal, followed by the text "alarm" or by the entry of an <alarm-type> followed by the text "alarm from" followed by a <device>. The <alarm-type> alternatives are all terminal alternatives, which are text entries as shown in the above grammar. The <alarm-type> alternatives may indicate the type of the alarm, e.g. "LOW_RESP_RATE" would indicate a low respiratory rate alarm.

The <count> symbol is satisfied by the alternatives "1 time" or <between-2-and-100> "times." The <between-2-and-100> times symbol is satisfied by the integers "2" through "100". The <duration> symbol is satisfied by a number of non-terminal symbols including <seconds>, <minutes>, <hours>, <minutes> <seconds>, <hours> <minutes> or <hours> <minutes> <seconds>. The <hours> symbol is satisfied by either "1 hour" or <between-2-and-24> followed by "hours" where <between-2-and-24> is satisfied by the integers "2" to "24". The <minutes> symbol is satisfied by the alternatives "1 minute" or <between-2-and-59> followed by "minutes" where <between-2-and-59> is satisfied by the integers "2" to "59". The <seconds> symbol is satisfied by either "1 second" or <between-2-and-59> followed by "seconds".

The <device> symbol is satisfied by the symbol <device-manufacturer> followed by <device-model>, where both <device-manufacturer> and <device-model> are satisfied by bracketed strings.

The <responses> symbol is satisfied by either the <response> symbol or a <response> followed by a comma and the <responses> symbol, thereby enabling the <response> symbol to comprise either a single response or more than one response. The <response> symbol is satisfied by a plurality of response alternatives, which can include both terminal symbols and non-terminal symbols. As shown in the exemplary grammar, the response alternatives may include terminal symbol instructions such as an instruction to update the central monitor, an issuance of a remote notification, a decreasing of the infusion rate of a pump by a set percentage or a pausing of an infusion. Non-terminal symbols may include the response alternative of switching to <algorithm-name>, which would enable the response alternative of switching to another algorithm. As described above, the <algorithm-name> is comprised of a bracketed string of characters. Alternatively, some of the terminal responses described above could be structured as non-terminal responses. For example, the responses relating to decreasing the infusion rate could be structured as "DECREASE_INFUSION_RATE_BY" <percentage-change> "percent" where <percentage-change> is satisfied by the integers "1" to "99".

An interface for creating rule sets is shown in FIG. 4 as 500. A first field 502, shown as the "Name" field, is provided for receiving entry of the medical delivery system rule set name. A second field 504, shown as the "Parameters" field, is provided for receiving a selection of a parameter and an associated condition, for example, "High ETCO$_2$ alarm occurs." Function buttons, 506, 508, 510, 512 are provided for receiving an input from a user to add, delete, modify or group the parameters and conditions. A third field 514, shown as the "Responses" field, is provided for receiving an authorized user's selection of the desired responses. As shown in FIG. 4, the responses may include updating a central monitor, issuing a remote notification to a caregiver, adjusting the infusion rate of a medication delivery pump, and/or switching to an alternative or different rule set.

In another aspect of the invention, once an authorized user has constructed the rule set and stored that rule set on the rule set configuration processor 140 and/or the central memory 135, the rule set may be selected by a caregiver and used to monitor the patient and patient care equipment system 100. The rule sets may be cataloged, grouped, or cross-referenced in the central storage in a variety of ways, including but not limited to by patient type (for example, an adult versus a pediatric patient), drug name (for example, morphine) or drug type (for example, opiate, narcotic, antibiotic, or cardiac), or location or ward within the care facility, which is sometimes referred to as a clinical care area (CCA), (for example, intensive care unit or ICU versus Emergency). For example, the rule sets may be organized, named, or entitled by patient parameter, e.g. "Sleep Apnea,"; patient characteristic, e.g. "Pediatric"; monitored variables; infused drugs; estimated patient drug sensitivity based upon infusion history and patient age, weight, etc.; and/or history of invalid infusion pump alarms and/or actions.

Figure 5:
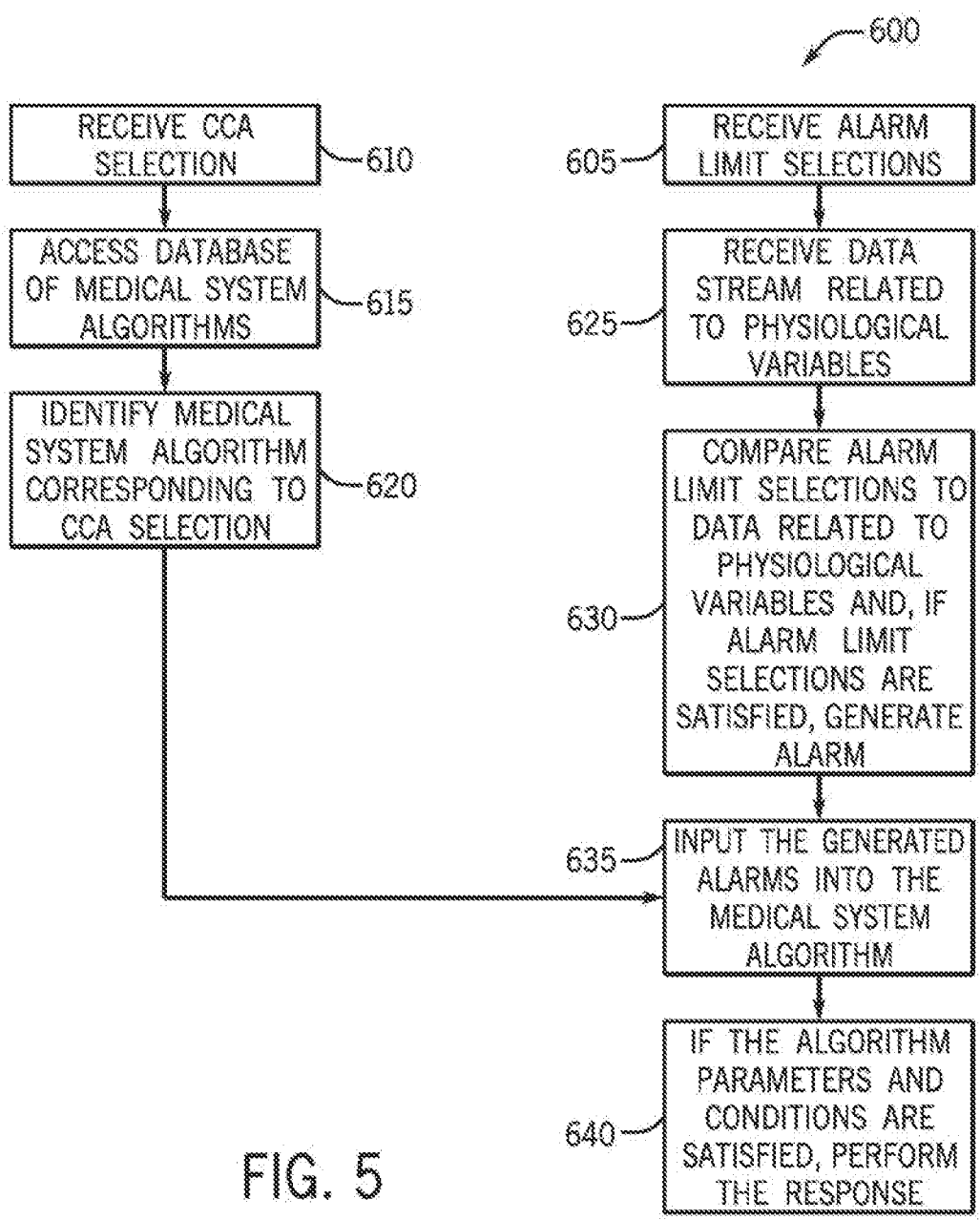
FIG. 5 is a flow chart of one embodiment of a system and method for selecting a rule set for use with a medication delivery device and patient monitoring system of the present invention.

As shown in FIG. 5, via any of the processors in the system 100 either the medical delivery pump 130 or the patient monitor 120, or both, can receive alarm limit selections input by a caregiver in step 605. As shown in step 610, the medical delivery pump input receives a particular group of rule sets, such as a particular clinical care area or all CCAs, based upon a selection input by the caregiver. In step 615, the processor 125 then accesses a database of rule sets stored on the central memory 135 that are correlated to the selection of the caregiver. In step 620, the caregiver selects the appropriate rule set; or, if only one rule set is returned, that rule set is implemented. In step 625, the patient monitor 120, and optionally the pump 130, receives the patient physiological information from the biometric sensors. The patient monitor and/or pump processor(s) compare the received physiological information, and if the alarm limits are exceeded, generate an alarm signal, which is sent to the patient monitor interface and rule set processor 125 as shown in step 630. The alarms and/or the physiological data and/or the monitored equipment data are processed according to the rule set as shown in step 635. If the rule set parameters and conditions are met, the patient monitor interface and rule set processor 125 outputs (or executes, in the case of an alternative or different rule set) the designated response or responses in step 640.

An example of a rule set configured to implement a series of new or different rule sets follows. In the case of PCA monitoring, three rule sets may be provided which respond to alarms associated with a patient's respiratory rate and ETCO$_2$ level. The first rule includes the parameter that one of the two alarms must be active for a minimum of 30 seconds prior to an action (e.g., pausing drug infusion). The second rule has a more restrictive parameter in which both alarms must be active for a minimum of 30 seconds prior to an action. The third rule defines the parameter for an infusion pause as an active ETCO$_2$ alarm for more than thirty seconds.

Although the clinician begins the PCA program using the first rule set, generation of two successive invalid pause events will lead to a change to the second rule at the time the second event is identified as invalid. This change could be automatic, in the case where the response specifies that the rule set be switched, or it could merely be suggested in the case where the rule set is configured to suggest to the caregiver that he or she switch rule sets. Similarly, if the two or more successive alarms are associated with only respiratory rate, the rule set could suggest through the pump interface that the clinician enable the third rule set. In this manner a series of rules sets are linked providing greater or lesser sensitivity to externally generated alarms. Suggestions for shifts between rule sets or changes to existing rule sets could also be generated to system administrators based on information acquired during the operation of the system.

An example of an application of a rule set in which a patient's recorded history of infusion events is used as a condition follows. To detect the potential for respiratory distress, a patient's respiratory rate and $ETCO_2$ are assessed using a respiratory monitor and a caregiver sets limits to 3-60 breaths per minute or bpm and 8-60 mmHg respectively, beyond which an alarm will be produced. With the respiratory monitor configured, the rule set is implemented within one of the processors described herein to reduce the number of false positives by requiring an alarm to be present for a minimum of 30 seconds AND within N time constants of a bolus infusion of the medication associated with respiratory distress. In this context, N is generally set to one (1) but can be modified depending upon the patient's age, disease status, co-morbidities and/or other constraints. For example, in the case of morphine delivery to a patient with liver disease, the standard time constant related to drug action is increased due to the lower metabolizing of the liver. The time constant is set to a default value associated with each drug.

Alternately, a status variable can be defined representing the patient drug load. The status variable can be used, in conjunction with individual alarms and a probability function, to improve the detection of a drug-induced adverse event and more specifically, respiratory depression. The drug load is estimated through the relationship:

Drug Load=Background Infusion+Summation (Bolus Dose*(time since dose)/(drug half-life))

Alternately, a first-order approximation for the pharmacokinetic drug elimination is:

Drug Load=Background Infusion+Summation (Bolus Dose*exp(−(time since dose)*(elimination rate constant)))

Where the elimination rate constant is estimated by the ln(2)/(half life).

In the simplest case, the function is a pre-set limit common to the particular drug. However, alternate functions can be used as well, including a percentage increase over time, a percentage increase over a pre-set limit, a sudden change in the rate of drug load, or other constraints. As a further alternative, fuzzy logic may be used to map the drug load to "high" or "low" and thereby qualify the output of the second alarm system as "probable" or "improbable". In the former situation, a rule set can be configured to create an alarm to a caregiver and to pause the delivery pump. In the latter situation, the rule set may be configured to only send an alarm to the caregiver.

In a further alternative, the drug load can be estimated as the mean drug consumption (MDC) over a period of time and used with the probability measures provided above.

In yet another example, the grammar disclosed above can be combined with both a drug infusion history for estimating the current patient drug load and the history of drug infusion requests. In particular, the demand to delivery ratio (D/D) and mean drug consumption (MDC) may be used as parameters in a rule set. A low MDC suggests alarms indicative of respiratory depression are likely invalid. However, when MDC is high, the D/D ratio is used to further qualify the drug infusion. When MDC is within 80% of maximum and D/D ratio is low (<1), the probability of a valid alarm event is likely. However, when the D/D ratio is high (>2), an indicator is provided suggesting the current pain medication is ineffective and therefore leading to high infusion rates and respiratory depression. Thus, both the calculated MDC and D/D ratio may be used in connection with respiratory rate as conditions in the rule set to provide further discrimination and decision support.

As mentioned herein, a response within a rule set can suggest or "recommend" to a caregiver to take certain actions related to the rule set and the parameters and conditions therein. For example, if a patient has not requested a PCA bolus for a twelve (12) hour period of time, the present system and method can be configured to allow an administrator or caregiver to configure a rule set to recommend to "change the therapy". Thus, the parameter that the administrator or caregiver could select would be "PCA Bolus Requests". The condition that the administrator or caregiver could select would be "None in 12 Hours". Alternative configurations could include the parameter being "No PCA Bolus Requests" and the condition being "In 12 Hours". Likewise, the response that the administrator or caregiver could select would be "Suggestion—Change Therapy [In View Of No PCA Bolus Requests In 12 Hours]". Other examples come to mind in view of the present example and description. The caregiver may either respond on their own accord or based on the system-generated suggestion respond by reduce the basal rate of infusion or wean the patient off of PCA therapy.

In another example, if a patient's pain scores are high (e.g., greater than 8 on a 10 point scale) and the patient PCA requests are frequent (e.g. more than ten (10) PCA denied events in a 4 hour period) then the present system and method can be configured to allow an administrator or caregiver to configure a rule set to recommend to "change the medication". Thus, the parameters that the administrator or caregiver could select would be "Average of Pain Scores" and "Denied PCA Bolus Requests". The Boolean operator that the administrator or caregiver could select would be an "AND" between the two parameters. The conditions the caregiver would select are "greater than 8" for the "Average Pain Scores" parameter and "More than ten (10) PCA denied events in four (4) hours" for the "Denied PCA Bolus Requests" parameter. Alternative configurations are possible. The response that the administrator or caregiver could select would be "Suggestion—Change Medication". Other examples come to mind in view of the present example and description. The caregiver may then, either on their own accord or based on the system-generated suggestion, respond by changing the medication. "Changing medication" can involve any one or a combination of the following: changing the program of the pump 130, changing to a different drug, or changing to a different drug concentration.

Any process descriptions or blocks in figures represented in the figures should be understood as representing modules, segments, or portions of code which include one or more executable instructions for implementing specific logical functions or steps in the process, and alternate implementations are included within the scope of the embodiments of the present invention in which functions may be executed out of order from that shown or discussed, including substantially concurrently or in reverse order, depending on the functionality involved, as would be understood by those having ordinary skill in the art.

Because of the interconnection of the various processors within the system 100, rule sets can be created or selected in a variety of locations within the system. By way of example and not limitation, rule sets can be created, modified, and saved at any processor in the system that has sufficient processing capability and access to memory for storage. By way of example and not limitation, rule sets can be selected on the patient monitor 120, on the pump or medication delivery device 130, on the patient monitor interface and rule set processor 125 or any combination thereof. The patient monitor interface and rule set processor 125 can be a communications engine located on the pump 130, on the patient monitor 120, on a separate module or shared between such components.

While the specific embodiments have been illustrated and described, numerous modifications come to mind without significantly departing from the invention. The scope of protection is only limited by the scope of the accompanying claims.

APPENDIX A

```
<alarm-integration-algorithm> ::=
    <algorithm-name>
    "is defined as when"
    <conditions>
    "do (" <responses> ")"
<algorithm-name> ::= <bracketed-string>
<conditions> ::=
    "(" <condition> ")" |
    "(" <conditions> ")" |
    <conditions> <boolean> <conditions>
    <condition> ::=
    <alarm> "occurs" |
    <alarm> "occurs" <count> "within a period of" <duration> |
    <alarm> "occurs and is not reset or cleared within" <duration> |
    <alarm> "does not occur for at least" |
    <duration> |
    "communication with" <device> "is lost" |
    "communication with" <device> "is restored"
<alarm> ::=
    <alarm-type> "alarm" |
    <alarm-type> "alarm from" <device>
<alarm-type> ::=
    "NO_BREATH" |
    "HIGH_ETCO2" |
    "LOW_ETCO2" |
    "HIGH_RESP_RATE" |
    "LOW_RESP_RATE" |
    "HI_FICO2" |
    "NO_PULSE" |
    "HIGH_PULSE_RATE" |
    "LOW_PULSE_RATE" |
    "LOW_SPO2" |
    "SPO2_SENSOR_OFF_PATIENT" |
    "SPO2_SENSOR_DISCONNECTED"
<device> ::=
    <device-manufacturer> <device-model>
<device-manufacturer> ::=
    <bracketed-string>
<device-model> ::=
    <bracketed-string>
<responses> ::=
    <response> |
    <response> "," <responses>
<response> ::=
    "UPDATE_CENTRAL_MONITOR" |
    "ISSUE REMOTE_NOTIFICATION" |
    "DECREASE_INFUSION_RATE_BY_25%" |
    "DECREASE_INFUSION_RATE_BY_50%" |
    "DECREASE_INFUSION_RATE_BY_75%" |
    "PAUSE_INFUSION" |
    "SWITCH_ALGORITHM_TO" <algorithm-name>
<boolean> ::=
```

APPENDIX A-continued

```
    "and" | "or"
<bracketed-string> ::=
    "[" <string> "]"
<string> ::=
    <char> |
    <char> <string>
<char> ::=
    <letter> |
    <digit> |
    <space>
<letter> ::=
    "a" | "b" | ... | "z" |
    "A" | "B" | ... | "Z"
<digit> ::=
    "0" | "1" | ... | "9"
<space> ::=
    " "
<count> ::=
    "1 time" |
    <between-2-and-100> "times"
<duration> ::=
    <hours> <minutes> <seconds> |
    <hours> <minutes> |
    <hours> <seconds> |
    <minutes> <seconds> |
    <hours> |
    <minutes> |
    <seconds>
<hours> ::=
    "1 hour" |
    <between-2-and-24> "hours"
<minutes> ::=
    "1 minute" |
    <between-2-and-59> "minutes"
<seconds> ::=
    "1 second" |
    <between-2-and-59> "seconds"
<between-2-and-100> ::= "2" | "3" | ... | "100"
<between-2-and-59> ::= "2" | "3" | ... | "59"
```

One exemplary simple rule according to the grammar is listed below.

```
[Simple rule set ]
    is defined as when
        (HIGH_ETCO2 alarm occurs)
    do
        (PAUSE_INFUSION)
```

Another such more complicated exemplary rule set that has several parameters as well as several responses according to the grammar listed below.

```
[More complicated rule set with multiple responses]
    is defined as when
        (
            (
                (HIGH_ETCO2 alarm occurs) or
                (LOW_RESP_RATE alarm occurs) or
                (LOW_SPO2 alarm occurs and is not reset or cleared within 5
                minutes )
            )
            or
            (communication with patient monitor is lost)
        )
    do
        (
            PAUSE_INFUSION,
            ISSUE_REMOTE_NOTIFICATION,
            UPDATE_CENTRAL_MONITOR
        )
```

What is claimed is:

1. A patient care system comprising:
one or more sensors for sensing at least one physiologic condition;
a medication delivery device configured to deliver a medicine to a patient;
a processor in communication with the one or more sensors and the medication delivery device, the processor configured to:
provide a context free grammar to define a medical system algorithm, the grammar comprising non-terminal parameter symbols and terminal parameter symbols that are configured to be satisfied by a plurality of non-terminal medical system parameters and terminal medical system parameters, respectively, the grammar further comprising non-terminal condition symbols and terminal condition symbols that are configured to be satisfied by a plurality of nonterminal medical system conditions and terminal medical system conditions, respectively, the grammar further comprising a response symbol that is configured to be satisfied by a plurality of medical system responses;
receive a first parameter selection comprising at least of one of the non-terminal parameters or at least one of the terminal parameters, defined by the grammar;
receive a respective first medical system condition selection corresponding to the at least one of the non-terminal parameter symbol or terminal parameter symbol for the selected first parameter selection defined by the grammar;
receive a medical system response selection;
generate the medical system algorithm from the first parameter selection, the first medical system condition selection, and the medical system response selection; and
store the generated medical system algorithm for later use by an automated medical device.

2. The system of claim 1, wherein the first parameter selection comprises at least one of the non-terminal parameter symbols and at least one of the terminal parameter symbols defined by the grammar.

3. The system of claim 1, wherein the response symbol comprises one of a non-terminal response symbol and a terminal response symbol, wherein the response symbol is configured to be satisfied by non-terminal medical system responses and terminal medical system responses, respectively.

4. The system of claim 1, wherein the medical system response selection comprises a non-terminal medical system response.

5. The system of claim 1, wherein the processor is further configured to:
receive a second parameter selection comprising at least of one of the non-terminal parameter symbols or at least one of the terminal parameter symbols defined by the grammar; and,
receive a respective second medical system condition selection corresponding to the at least one of the non-terminal parameter symbol or terminal parameter symbol for the selected second parameter selection defined by the grammar.

6. The system of claim 5, wherein the second parameter selection comprises at least one of the non-terminal parameter symbols and at least one of the terminal parameter symbols defined by the grammar.

7. The system of claim 5, wherein the first medical system parameter selection is a first alarm selection and wherein the second medical system parameter selection is a second alarm selection, different than the first alarm selection.

8. The system of claim 7, wherein the first alarm selection is for an alarm related to a medicine delivery device function and wherein the second alarm selection is for an alarm related to a patient monitor function.

9. The system of claim 8, wherein the alarm related to the medicine delivery device function is one of a loss of communication with the medicine delivery device alarm and status of medicine delivery device parameter alarm.

10. The system of claim 8, wherein the alarm related to the patient monitor function is one of a loss of communication with the patient monitor alarm and status of a patient monitor parameter alarm.

11. The system of claim 7, wherein the first medical system parameter selection is a first alarm selection.

12. The system of claim 11, wherein the first alarm selection is one of an alarm related to a medicine delivery device function and wherein the second alarm selection is for an alarm related to a patient monitor function.

13. The system of claim 1, wherein the first medical system parameter is a component of a medical system condition.

14. The system of claim 1, wherein the processor is further configured to receiving a first Boolean connector selection, wherein the generated medical system algorithm is further generated from the first Boolean connector selection.

15. The claim of 14, wherein the processor is further configured to receive a second Boolean connector selection, wherein the medical system algorithm is further generated from the second Boolean connector selection.

16. The system of claim 1, wherein the medical system parameters are alternative medical system parameters within the grammar, wherein the alternative medical parameters do not represent a medical state or condition of a patient.

17. The system of claim 1, wherein at least one of the medical system parameters defined by the grammar comprises both terminal and non-terminal components.

18. The system of claim 1, wherein the processor is configured to receive a plurality of medical system response selections, the plurality of medical system response selections comprising the medical response selection.

19. The system of claim 1, wherein the first medical system parameter selection is received through a first region of a user interface display and wherein the medical system response selection is received through a second region of the user interface display.

20. The system of claim 16, wherein at least one of the alternative medical system parameters defined by the grammar comprises a change in communication state with a medical device.

* * * * *

UNITED STATES PATENT AND TRADEMARK OFFICE
CERTIFICATE OF CORRECTION

PATENT NO. : 12,036,390 B2
APPLICATION NO. : 18/300839
DATED : July 16, 2024
INVENTOR(S) : Steven R. Wehba et al.

It is certified that error appears in the above-identified patent and that said Letters Patent is hereby corrected as shown below:

On the Title Page

Page 12, Column 2 (Other Publications), Line 56, delete "EXRI" and insert -- ECRI --.

Page 13, Column 1 (Other Publications), Line 19, delete "Informations" and insert -- Information --.

Page 14, Column 1 (Other Publications), Line 26, delete "Octover" and insert -- October --.

In the Specification

Column 1, Line 6, delete "APPLICTIONS" and insert -- APPLICATIONS --.

Column 1, Line 20 (approx.), delete "61/170,205" and insert -- 61/170,205, --.

Column 4, Line 27, delete "MASSIMO" and insert -- MASIMO --.

Column 10, Line 40, delete "FIGS." and insert -- FIG. --.

Column 12, Line 32, delete "Format" and insert -- Form --.

Column 12, Line 44, delete "I" and insert -- | --.

In the Claims

Column 19, Line 19, Claim 1, delete "nonterminal" and insert -- non-terminal --.

Column 20, Line 37, Claim 15, delete "claim of" and insert -- system of claim --.

Signed and Sealed this
Seventeenth Day of September, 2024

Katherine Kelly Vidal
*Director of the United States Patent and Trademark Office*